(12) United States Patent
DiVito et al.

(10) Patent No.: US 11,684,421 B2
(45) Date of Patent: *Jun. 27, 2023

(54) DENTAL AND MEDICAL TREATMENTS AND PROCEDURES

(71) Applicant: PIPSTEK, LLC, Laguna Hills, CA (US)

(72) Inventors: Enrico E. DiVito, Scottsdale, AZ (US); Douglas L. Glover, Phoenix, AZ (US); Kemmons A. Tubbs, Mesa, AZ (US); Mark P. Colonna, Whitefish, MT (US)

(73) Assignee: PIPSTEK, LLC, Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/898,340

(22) Filed: Aug. 29, 2022

(65) Prior Publication Data
US 2022/0409278 A1    Dec. 29, 2022

Related U.S. Application Data

(63) Continuation of application No. 17/317,744, filed on May 11, 2021, now Pat. No. 11,426,239, which is a
(Continued)

(51) Int. Cl.
*A61B 18/26* (2006.01)
*A61C 1/00* (2006.01)
(Continued)

(52) U.S. Cl.
CPC ............ *A61B 18/26* (2013.01); *A61C 1/0046* (2013.01); *A61C 5/40* (2017.02); *A61N 5/0624* (2013.01);
(Continued)

(58) Field of Classification Search
CPC .... A61C 5/40; A61C 5/46; A61C 5/50; A61C 1/0046; A61B 18/26; A61B 18/20; A61B 2018/263; A61N 5/0624; A61N 2005/0606

See application file for complete search history.

(56) References Cited

U.S. PATENT DOCUMENTS

| 1,500,107 A | 7/1924 | Chandler |
| 2,108,558 A | 2/1938 | Jackman |

(Continued)

FOREIGN PATENT DOCUMENTS

| CA | 2031739 | 6/1991 |
| CA | 2771397 | 2/2011 |

(Continued)

OTHER PUBLICATIONS

U.S. Appl. No. 16/160,799, filed Oct. 15, 2018, Bergheim et al.
(Continued)

*Primary Examiner* — Jacqueline T Johanas
*Assistant Examiner* — Shannel Nicole Belk
(74) *Attorney, Agent, or Firm* — Knobbe, Martens, Olson & Bear LLP

(57) ABSTRACT

A method treating a root canal in a tooth by introducing into the pulp chamber of a tooth and pulsing a laser light into the fluid reservoir so as to disintegrate pulp within the root canal without generation of any significant heat in said liquid fluid so as to avoid elevating the temperature of any of the dentin, tooth, or other adjacent tissue more than about 5° C.

17 Claims, 9 Drawing Sheets

Related U.S. Application Data continuation of application No. 14/537,742, filed on Nov. 10, 2014, which is a continuation-in-part of application No. 14/077,880, filed on Nov. 12, 2013, now abandoned, which is a continuation of application No. 13/633,096, filed on Oct. 1, 2012, now abandoned, which is a continuation of application No. 12/875,565, filed on Sep. 3, 2010, now abandoned, which is a continuation-in-part of application No. 12/395,643, filed on Feb. 28, 2009, now Pat. No. 7,980,854, which is a continuation-in-part of application No. 11/895,404, filed on Aug. 24, 2007, now abandoned, said application No. 12/875,565 is a continuation-in-part of application No. 11/895,404, filed on Aug. 24, 2007, now abandoned, which is a continuation-in-part of application No. 11/704,655, filed on Feb. 9, 2007, now Pat. No. 7,959,441, said application No. 12/395,643 is a continuation-in-part of application No. 11/704,655, filed on Feb. 9, 2007, now Pat. No. 7,959,441.

(60) Provisional application No. 60/840,282, filed on Aug. 24, 2006, provisional application No. 60/840,282, filed on Aug. 24, 2006.

(51) Int. Cl.
  *A61C 5/40* (2017.01)
  *A61N 5/06* (2006.01)
  *A61N 7/02* (2006.01)
  *A61N 5/067* (2006.01)
  *A61B 18/00* (2006.01)

(52) U.S. Cl.
  CPC .... *A61N 7/022* (2013.01); *A61B 2018/00565* (2013.01); *A61B 2018/263* (2013.01); *A61N 5/067* (2021.08); *A61N 2005/0606* (2013.01); *A61N 2005/0631* (2013.01)

(56) References Cited

U.S. PATENT DOCUMENTS

| | | |
|---|---|---|
| 3,023,306 A | 2/1962 | Kester |
| 3,225,759 A | 12/1965 | Drapen et al. |
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,593,423 A | 7/1971 | Jones et al. |
| 3,624,907 A | 12/1971 | Brass et al. |
| 3,703,170 A | 11/1972 | Ryckman, Jr. |
| 3,731,675 A | 5/1973 | Kelly |
| 3,739,983 A | 6/1973 | Jousson |
| 3,745,655 A | 7/1973 | Malmin |
| 3,747,216 A | 7/1973 | Bassi et al. |
| 3,756,225 A | 9/1973 | Moret et al. |
| 3,828,770 A | 8/1974 | Kuris et al. |
| 3,871,099 A | 3/1975 | Kahn |
| 3,921,296 A | 11/1975 | Harris |
| 3,930,505 A | 1/1976 | Wallach |
| 3,962,790 A | 6/1976 | Riitano et al. |
| 4,021,921 A | 5/1977 | Detaille |
| 4,060,600 A | 11/1977 | Vit |
| 4,071,956 A | 2/1978 | Andress |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,330,278 A | 5/1982 | Martin |
| 4,376,835 A | 3/1983 | Schmitt et al. |
| 4,386,911 A | 6/1983 | Maloney et al. |
| 4,424,036 A | 1/1984 | Lokken |
| 4,474,251 A | 2/1984 | Johnson, Jr. |
| 4,462,803 A | 7/1984 | Landgraff et al. |
| 4,492,575 A | 1/1985 | Mabille |
| 4,522,597 A | 6/1985 | Gallant |
| 4,534,542 A | 8/1985 | Russo |
| 4,539,987 A | 9/1985 | Nath et al. |
| 4,554,088 A | 11/1985 | Whitehead et al. |
| 4,595,365 A | 6/1986 | Edel et al. |
| 4,608,017 A | 8/1986 | Sadohara |
| 4,659,218 A | 4/1987 | de Lasa et al. |
| 4,661,070 A | 4/1987 | Friedman |
| 4,671,259 A | 6/1987 | Kirchner |
| 4,676,586 A | 6/1987 | Jones et al. |
| 4,676,749 A | 6/1987 | Mabille |
| 4,684,781 A | 8/1987 | Frish et al. |
| 4,732,193 A | 3/1988 | Gibbs |
| 4,789,335 A | 12/1988 | Geller et al. |
| 4,818,230 A | 4/1989 | Myers et al. |
| 4,872,837 A | 10/1989 | Issalene et al. |
| 4,917,603 A | 4/1990 | Haack |
| 4,935,635 A | 6/1990 | O'Harra |
| 4,941,459 A | 7/1990 | Mathur |
| 4,957,436 A | 9/1990 | Ryder |
| 4,973,246 A | 11/1990 | Black et al. |
| 4,985,027 A | 1/1991 | Dressel |
| 4,992,048 A | 2/1991 | Goof |
| 4,993,947 A | 2/1991 | Grosrey |
| 5,013,300 A | 5/1991 | Williams |
| 5,020,995 A | 6/1991 | Levy |
| 5,029,576 A | 7/1991 | Evans, Sr. |
| 5,037,431 A | 8/1991 | Summers et al. |
| 5,046,950 A | 9/1991 | Favonio |
| 5,055,048 A | 10/1991 | Vassiliadis et al. |
| 5,066,232 A | 11/1991 | Negri et al. |
| 5,094,256 A | 3/1992 | Barth |
| 5,112,224 A | 5/1992 | Shirota |
| 5,116,227 A * | 5/1992 | Levy .................. A61C 5/40 606/7 |
| 5,118,293 A | 6/1992 | Levy |
| 5,122,060 A | 6/1992 | Vassiliadis et al. |
| 5,123,845 A | 6/1992 | Vassiliadis et al. |
| 5,151,029 A | 9/1992 | Levy |
| 5,151,031 A | 9/1992 | Levy |
| 5,169,318 A | 12/1992 | Levy |
| 5,171,150 A | 12/1992 | Levy |
| 5,173,049 A | 12/1992 | Levy |
| 5,173,050 A | 12/1992 | Dillon |
| 5,180,304 A | 1/1993 | Vassiliadis et al. |
| 5,188,532 A | 2/1993 | Levy |
| 5,188,634 A | 2/1993 | Hussein et al. |
| 5,194,005 A | 3/1993 | Levy |
| 5,194,723 A | 3/1993 | Cates et al. |
| 5,195,952 A | 3/1993 | Solnit et al. |
| 5,224,942 A | 7/1993 | Beuchat et al. |
| 5,228,852 A | 7/1993 | Goldsmith et al. |
| 5,232,366 A | 8/1993 | Levy |
| 5,232,367 A | 8/1993 | Vassiliadis et al. |
| 5,236,360 A | 8/1993 | Levy |
| 5,249,964 A | 10/1993 | Levy |
| 5,257,935 A | 11/1993 | Vassiliadis et al. |
| 5,267,856 A | 12/1993 | Wolbarsht et al. |
| 5,267,995 A | 12/1993 | Doiron et al. |
| 5,269,777 A | 12/1993 | Doiron et al. |
| 5,273,713 A | 12/1993 | Levy |
| 5,275,564 A | 1/1994 | Vassiliadis et al. |
| 5,281,141 A | 1/1994 | Kowalyk |
| 5,290,274 A | 3/1994 | Levy et al. |
| 5,292,253 A | 3/1994 | Levy |
| 5,295,828 A | 3/1994 | Grosrey |
| 5,304,167 A | 4/1994 | Freiberg |
| 5,306,143 A | 4/1994 | Levy |
| 5,307,839 A | 5/1994 | Loebker et al. |
| 5,310,344 A | 5/1994 | Vassiliadis et al. |
| 5,318,562 A | 6/1994 | Levy et al. |

(56) References Cited

U.S. PATENT DOCUMENTS

| | | | |
|---|---|---|---|
| 5,322,504 A | 6/1994 | Doherty et al. | |
| 5,324,200 A | 6/1994 | Vassiliadis et al. | |
| 5,326,263 A | 7/1994 | Weissman | |
| 5,326,264 A | 7/1994 | Al Kasem | |
| 5,334,016 A | 8/1994 | Goldsmith et al. | |
| 5,334,019 A | 8/1994 | Goldsmith et al. | |
| 5,342,196 A | 8/1994 | Van Hale | |
| 5,342,198 A | 8/1994 | Vassiliadis et al. | |
| 5,374,266 A | 12/1994 | Kataoka et al. | |
| 5,380,201 A | 1/1995 | Kawata | |
| 5,387,376 A | 2/1995 | Gasser | |
| 5,390,204 A | 2/1995 | Yessik et al. | |
| D356,866 S | 3/1995 | Meller | |
| 5,399,089 A | 3/1995 | Eichman et al. | |
| 5,409,376 A | 4/1995 | Murphy | |
| 5,415,652 A | 5/1995 | Mueller et al. | |
| 5,422,899 A | 6/1995 | Freiberg et al. | |
| 5,428,699 A | 6/1995 | Pon | |
| 5,435,724 A | 7/1995 | Goodman et al. | |
| 5,474,451 A | 12/1995 | Dalrymple et al. | |
| 5,484,283 A | 1/1996 | Franetzki | |
| 5,490,779 A | 2/1996 | Malmin | |
| 5,503,559 A | 4/1996 | Vari | |
| 5,507,739 A | 4/1996 | Vassiliadis et al. | |
| 5,540,587 A | 7/1996 | Malmin | |
| 5,545,039 A | 8/1996 | Mushabac | |
| 5,547,376 A | 8/1996 | Harrel | |
| 5,554,896 A | 9/1996 | Hogan | |
| 5,562,692 A | 10/1996 | Bair | |
| 5,564,929 A | 10/1996 | Alpert | |
| 5,570,182 A | 10/1996 | Nathel et al. | |
| 5,591,184 A | 1/1997 | McDonnell et al. | |
| 5,601,430 A | 2/1997 | Kutsch et al. | |
| 5,611,797 A | 3/1997 | George | |
| 5,620,414 A | 4/1997 | Campbell, Jr. | |
| 5,621,745 A | 4/1997 | Yessik et al. | |
| 5,622,501 A | 4/1997 | Levy | |
| 5,639,239 A | 6/1997 | Earle | |
| 5,642,997 A | 7/1997 | Gregg et al. | |
| 5,643,299 A | 7/1997 | Bair | |
| 5,660,817 A | 8/1997 | Masterman et al. | |
| 5,662,501 A | 9/1997 | Levy | |
| 5,674,226 A | 10/1997 | Doherty et al. | |
| 5,688,486 A | 11/1997 | Watson et al. | |
| 5,720,894 A | 2/1998 | Neev et al. | |
| 5,730,727 A | 3/1998 | Russo | |
| 5,735,815 A | 4/1998 | Bair | |
| 5,740,291 A | 4/1998 | De Lasa et al. | |
| 5,741,247 A | 4/1998 | Rizoiu et al. | |
| 5,748,655 A | 5/1998 | Yessik et al. | |
| 5,755,752 A | 5/1998 | Segal | |
| 5,759,031 A | 6/1998 | Goldsmith et al. | |
| 5,759,159 A | 6/1998 | Masreliez | |
| 5,762,501 A | 6/1998 | Levy | |
| 5,785,521 A | 7/1998 | Rizoiu et al. | |
| 5,795,153 A | 8/1998 | Rechmann | |
| 5,797,745 A | 8/1998 | Ruddle | |
| 5,810,037 A | 9/1998 | Sasaki et al. | |
| 5,816,807 A | 10/1998 | Matsutani et al. | |
| 5,820,373 A | 10/1998 | Okano et al. | |
| 5,825,958 A | 10/1998 | Gollihar et al. | |
| 5,832,013 A | 11/1998 | Yessik et al. | |
| 5,839,896 A | 11/1998 | Hickok et al. | |
| 5,842,863 A | 12/1998 | Bruns et al. | |
| 5,846,080 A | 12/1998 | Schneider | |
| 5,853,384 A | 12/1998 | Bair | |
| 5,865,790 A | 2/1999 | Bair | |
| 5,868,570 A | 2/1999 | Hickok et al. | |
| 5,874,677 A | 2/1999 | Bab et al. | |
| 5,879,160 A | 3/1999 | Ruddle | |
| 5,885,082 A | 3/1999 | Levy | |
| 5,897,314 A | 4/1999 | Hack et al. | |
| 5,911,711 A | 6/1999 | Pelkey | |
| 5,915,965 A | 6/1999 | Ohlsson et al. | |
| 5,921,775 A | 7/1999 | Buchanan | |
| 5,968,037 A | 10/1999 | Rizoiu et al. | |
| 5,968,039 A | 10/1999 | Deutsch | |
| 5,971,755 A | 10/1999 | Liebermann et al. | |
| 5,975,897 A | 11/1999 | Propp et al. | |
| 5,989,023 A | 11/1999 | Summer et al. | |
| 6,004,319 A | 12/1999 | Goble et al. | |
| 6,019,605 A | 2/2000 | Myers | |
| 6,022,309 A | 2/2000 | Celliers et al. | |
| 6,030,221 A | 2/2000 | Jones et al. | |
| 6,033,431 A | 3/2000 | Segal | |
| 6,045,516 A | 4/2000 | Phelan | |
| 6,053,735 A | 4/2000 | Buchanan | |
| 6,079,979 A | 6/2000 | Riitano | |
| 6,086,367 A | 7/2000 | Levy | |
| 6,096,029 A | 8/2000 | O'Donnell, Jr. | |
| 6,104,853 A | 8/2000 | Miyagi et al. | |
| 6,106,514 A | 8/2000 | O'Donnell, Jr. | |
| 6,122,300 A | 9/2000 | Frieberg et al. | |
| 6,129,721 A | 10/2000 | Kataoka et al. | |
| 6,139,319 A | 10/2000 | Sauer et al. | |
| 6,139,320 A | 10/2000 | Hahn | |
| 6,143,011 A | 11/2000 | Hood et al. | |
| D435,651 S | 12/2000 | Hartwein | |
| 6,159,006 A | 12/2000 | Cook et al. | |
| 6,162,052 A * | 12/2000 | Kokubu | A61B 18/22 433/29 |
| 6,162,177 A | 12/2000 | Bab et al. | |
| 6,162,202 A | 12/2000 | Sicurelli et al. | |
| 6,164,966 A | 12/2000 | Turdiu et al. | |
| 6,179,617 B1 | 1/2001 | Ruddle | |
| 6,190,318 B1 | 2/2001 | Bab et al. | |
| 6,197,020 B1 | 3/2001 | O'Donnell, Jr. | |
| 6,221,031 B1 | 4/2001 | Heraud | |
| 6,224,378 B1 | 5/2001 | Valdes et al. | |
| 6,227,855 B1 | 5/2001 | Hickok et al. | |
| 6,231,567 B1 | 5/2001 | Rizoiu et al. | |
| 6,245,032 B1 | 6/2001 | Sauer et al. | |
| 6,254,597 B1 | 7/2001 | Rizoiu et al. | |
| 6,270,342 B1 | 8/2001 | Neuberger et al. | |
| 6,282,013 B1 | 8/2001 | Ostler et al. | |
| 6,288,499 B1 | 9/2001 | Rizoiu et al. | |
| 6,290,502 B1 | 9/2001 | Hugo | |
| 6,309,340 B1 | 10/2001 | Nakagawa | |
| 6,312,440 B1 | 11/2001 | Hood et al. | |
| 6,315,557 B1 | 11/2001 | Messick | |
| 6,315,565 B1 | 11/2001 | Slotke et al. | |
| 6,319,002 B1 | 11/2001 | Pond | |
| 6,343,929 B1 | 2/2002 | Fischer | |
| 6,350,123 B1 | 2/2002 | Rizoiu et al. | |
| 6,354,660 B1 | 3/2002 | Friedrich | |
| 6,386,871 B1 | 5/2002 | Rossell | |
| 6,389,193 B1 | 5/2002 | Kimmel et al. | |
| 6,390,815 B1 | 5/2002 | Pond | |
| 6,428,319 B1 | 8/2002 | Lopez et al. | |
| 6,440,103 B1 | 8/2002 | Hood et al. | |
| 6,454,566 B1 | 9/2002 | Lynch et al. | |
| 6,464,498 B2 | 10/2002 | Pond | |
| 6,485,304 B2 | 11/2002 | Beerstecher et al. | |
| 6,497,572 B2 | 12/2002 | Hood et al. | |
| 6,511,493 B1 | 1/2003 | Moutafis et al. | |
| 6,514,077 B1 | 2/2003 | Wilk | |
| 6,527,766 B1 | 3/2003 | Bair | |
| 6,533,775 B1 | 3/2003 | Rizoiu | |
| 6,538,739 B1 | 3/2003 | Visuri et al. | |
| 6,544,256 B1 | 4/2003 | Rizoiu et al. | |
| 6,561,803 B1 | 5/2003 | Rizoiu et al. | |
| 6,562,050 B1 | 5/2003 | Owen | |
| 6,567,582 B1 | 5/2003 | Rizoiu et al. | |
| 6,572,709 B1 | 6/2003 | Kaneda et al. | |
| 6,592,371 B2 | 7/2003 | Durbin et al. | |
| 6,602,074 B1 | 8/2003 | Suh et al. | |
| 6,610,053 B1 | 8/2003 | Rizoiu et al. | |
| 6,616,447 B1 | 9/2003 | Rizoiu et al. | |
| 6,616,451 B1 | 9/2003 | Rizoiu et al. | |
| 6,638,219 B1 | 10/2003 | Asch et al. | |
| 6,641,394 B2 | 11/2003 | Garman | |
| 6,644,972 B1 | 11/2003 | Mays | |
| 6,663,386 B1 | 12/2003 | Moelsgaard | |
| 6,669,685 B1 | 12/2003 | Rizoiu et al. | |

(56) References Cited

U.S. PATENT DOCUMENTS

| | | |
|---|---|---|
| 6,676,409 B2 | 1/2004 | Grant |
| 6,679,837 B2 | 1/2004 | Daikuzono |
| 6,744,790 B1 | 6/2004 | Tilleman et al. |
| 6,783,364 B1 | 8/2004 | Juan |
| 6,817,862 B2 | 11/2004 | Hickok |
| 6,821,272 B2 | 11/2004 | Rizoiu et al. |
| D499,486 S | 12/2004 | Kuhn et al. |
| 6,827,766 B2 | 12/2004 | Carnes et al. |
| 6,829,427 B1 | 12/2004 | Becker |
| 6,881,061 B2 | 4/2005 | Fisher |
| 6,886,371 B2 | 5/2005 | Arai et al. |
| 6,893,259 B1 | 5/2005 | Reizenson |
| 6,910,887 B2 | 6/2005 | Van Den Houdt |
| 6,942,658 B1 | 9/2005 | Rizoiu et al. |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,008,224 B1 | 3/2006 | Browning et al. |
| 7,011,521 B2 | 3/2006 | Sierro et al. |
| 7,011,644 B2 | 3/2006 | Andrew et al. |
| 7,014,465 B1 | 3/2006 | Marais |
| 7,029,278 B2 | 4/2006 | Pond |
| 7,044,737 B2 | 5/2006 | Fu |
| 7,068,912 B1 | 6/2006 | Becker |
| 7,090,497 B1 | 8/2006 | Harris |
| 7,108,693 B2 | 9/2006 | Rizoiu et al. |
| 7,115,100 B2 | 10/2006 | McRury et al. |
| 7,144,249 B2 | 12/2006 | Rizoiu et al. |
| 7,147,468 B2 | 12/2006 | Snyder et al. |
| 7,163,400 B2 | 1/2007 | Cozean et al. |
| 7,187,822 B2 | 3/2007 | Rizoiu et al. |
| 7,194,180 B2 | 3/2007 | Becker |
| 7,226,288 B2 | 6/2007 | Schoeffel |
| 7,234,937 B2 | 6/2007 | Sachdeva et al. |
| 7,238,342 B2 | 7/2007 | Torabinejad et al. |
| 7,261,558 B2 | 8/2007 | Rizoiu et al. |
| 7,261,561 B2 | 8/2007 | Ruddle et al. |
| 7,269,306 B1 | 9/2007 | Koeneman et al. |
| 7,270,544 B2 | 9/2007 | Schemmer et al. |
| 7,270,657 B2 | 9/2007 | Rizoiu et al. |
| 7,288,086 B1 | 10/2007 | Andriasyan |
| 7,290,940 B2 | 11/2007 | Boutoussov |
| 7,292,759 B2 | 11/2007 | Boutoussov et al. |
| 7,296,318 B2 | 11/2007 | Mourad et al. |
| 7,303,397 B2 | 12/2007 | Boutoussov |
| 7,306,459 B1 | 12/2007 | Williams et al. |
| 7,306,577 B2 | 12/2007 | Lemoine et al. |
| 7,320,594 B1 | 1/2008 | Rizoiu et al. |
| 7,326,054 B2 | 2/2008 | Todd et al. |
| 7,356,208 B2 | 4/2008 | Becker |
| 7,356,225 B2 | 4/2008 | Loebel |
| 7,384,419 B2 | 6/2008 | Jones et al. |
| 7,415,050 B2 | 8/2008 | Rizoiu et al. |
| 7,421,186 B2 | 9/2008 | Boutoussov et al. |
| 7,424,199 B2 | 9/2008 | Rizoiu et al. |
| 7,445,618 B2 | 11/2008 | Eggers et al. |
| 7,448,867 B2 | 11/2008 | Aloise et al. |
| 7,458,380 B2 | 12/2008 | Jones et al. |
| 7,461,658 B2 | 12/2008 | Jones et al. |
| 7,461,982 B2 | 12/2008 | Boutoussov et al. |
| 7,467,946 B2 | 12/2008 | Rizoiu et al. |
| 7,470,124 B2 | 12/2008 | Bornstein |
| 7,485,116 B2 | 2/2009 | Cao |
| 7,549,861 B2 | 6/2009 | Ruddle et al. |
| 7,563,226 B2 | 7/2009 | Boutoussov |
| 7,575,381 B2 | 8/2009 | Boutoussov |
| 7,578,622 B2 | 8/2009 | Boutoussov |
| 7,620,290 B2 | 11/2009 | Rizoiu et al. |
| 7,621,745 B2 | 11/2009 | Bornstein |
| 7,630,420 B2 | 12/2009 | Boutoussov |
| 7,641,668 B2 | 1/2010 | Perry et al. |
| 7,665,467 B2 | 2/2010 | Jones et al. |
| 7,670,141 B2 | 3/2010 | Thomas et al. |
| 7,695,469 B2 | 4/2010 | Boutoussov et al. |
| 7,696,466 B2 | 4/2010 | Rizoiu et al. |
| 7,697,814 B2 | 4/2010 | Rizoiu et al. |
| 7,702,196 B2 | 4/2010 | Boutoussov et al. |
| 7,748,979 B2 | 7/2010 | Nahlieli |
| 7,751,895 B2 | 7/2010 | Jones et al. |
| 7,766,656 B1 | 8/2010 | Feine |
| 7,778,306 B2 | 8/2010 | Marincek et al. |
| 7,815,630 B2 | 10/2010 | Rizoiu et al. |
| 7,817,687 B2 | 10/2010 | Rizoiu et al. |
| 7,833,016 B2 | 11/2010 | Gharib et al. |
| 7,833,017 B2 | 11/2010 | Hof et al. |
| 7,845,944 B2 | 12/2010 | DiGasbarro |
| 7,867,223 B2 | 1/2011 | Van Valen |
| 7,867,224 B2 | 1/2011 | Lukac et al. |
| 7,878,204 B2 | 2/2011 | Van Valen |
| 7,891,363 B2 | 2/2011 | Jones et al. |
| 7,891,977 B2 | 2/2011 | Riva |
| 7,901,373 B2 | 3/2011 | Tavger |
| 7,909,040 B2 | 3/2011 | Jones et al. |
| 7,909,817 B2 | 3/2011 | Griffin et al. |
| 7,916,282 B2 | 3/2011 | Duineveld et al. |
| 7,942,667 B2 | 5/2011 | Rizoiu et al. |
| 7,957,440 B2 | 6/2011 | Boutoussov |
| 7,959,441 B2 * | 6/2011 | Glover .................. A61C 1/0046 433/29 |
| 7,967,017 B2 | 6/2011 | Jones et al. |
| 7,970,027 B2 | 6/2011 | Rizoiu et al. |
| 7,970,030 B2 | 6/2011 | Rizoiu et al. |
| 7,980,854 B2 | 7/2011 | Glover et al. |
| 7,980,923 B2 | 7/2011 | Olmo et al. |
| 7,997,279 B2 | 8/2011 | Jones et al. |
| 7,998,136 B2 | 8/2011 | Jones et al. |
| 8,002,544 B2 | 8/2011 | Rizoiu et al. |
| 8,011,923 B2 | 9/2011 | Lukac et al. |
| 8,023,795 B2 | 9/2011 | Rizoiu et al. |
| 8,033,825 B2 | 10/2011 | Rizoiu et al. |
| 8,037,566 B2 | 10/2011 | Grez |
| 8,047,841 B2 | 11/2011 | Jefferies |
| 8,052,627 B2 | 11/2011 | Gromer et al. |
| 8,056,564 B2 | 11/2011 | Jones et al. |
| 8,062,673 B2 | 11/2011 | Figuly et al. |
| 8,100,482 B2 | 1/2012 | Kito et al. |
| 8,128,401 B2 | 3/2012 | Ruddle et al. |
| 8,152,797 B2 | 4/2012 | Boutoussov et al. |
| 8,204,612 B2 | 6/2012 | Feine et al. |
| 8,221,117 B2 | 7/2012 | Rizoiu et al. |
| 8,235,719 B2 | 8/2012 | Ruddle et al. |
| 8,241,035 B2 | 8/2012 | Jones et al. |
| 8,256,431 B2 | 9/2012 | Van Valen |
| D669,180 S | 10/2012 | Takashi et al. |
| 8,276,593 B2 | 10/2012 | Jones et al. |
| 8,295,025 B2 | 10/2012 | Edel et al. |
| 8,297,540 B1 | 10/2012 | Vijay |
| 8,298,215 B2 | 10/2012 | Zinn |
| 8,317,514 B2 | 11/2012 | Weill |
| 8,322,910 B2 | 12/2012 | Gansmuller et al. |
| 8,328,552 B2 | 12/2012 | Ruddle |
| 8,366,702 B2 | 2/2013 | Van Valen |
| 8,371,848 B2 | 2/2013 | Okawa et al. |
| 8,388,345 B2 | 3/2013 | Ruddle |
| 8,403,922 B2 | 3/2013 | Boutoussov et al. |
| 8,419,719 B2 | 4/2013 | Rizoiu et al. |
| 8,439,676 B2 | 5/2013 | Florman |
| 8,439,904 B2 | 5/2013 | Jones et al. |
| 8,448,645 B2 | 5/2013 | Jones et al. |
| 8,470,035 B2 | 6/2013 | Cruise et al. |
| 8,474,635 B2 | 7/2013 | Johnson |
| 8,479,745 B2 | 7/2013 | Rizoiu |
| 8,485,818 B2 | 7/2013 | Boutoussov et al. |
| 8,506,293 B2 | 8/2013 | Pond |
| 8,525,059 B2 | 9/2013 | Berger et al. |
| 8,544,473 B2 | 10/2013 | Rizoiu et al. |
| 8,568,392 B2 | 10/2013 | Jones et al. |
| 8,588,268 B2 | 11/2013 | Boutoussov et al. |
| 8,602,033 B2 | 12/2013 | Jones et al. |
| 8,603,079 B2 | 12/2013 | Van Valen |
| 8,617,090 B2 | 12/2013 | Fougere et al. |
| 8,653,392 B2 | 2/2014 | Berger et al. |

(56) References Cited

U.S. PATENT DOCUMENTS

| | | |
|---|---|---|
| 8,672,678 B2 | 3/2014 | Gramann et al. |
| D701,971 S | 4/2014 | Van Valen et al. |
| 8,684,956 B2 | 4/2014 | McDonough et al. |
| 8,709,057 B2 | 4/2014 | Tettamanti et al. |
| RE44,917 E | 5/2014 | Tuttle |
| 8,740,957 B2 | 6/2014 | Masotti |
| 8,747,005 B2 | 6/2014 | Kemp et al. |
| 8,753,121 B2 | 6/2014 | Gharib et al. |
| 8,758,010 B2 | 6/2014 | Yamanaka et al. |
| 8,764,739 B2 | 7/2014 | Boutoussov et al. |
| 8,792,251 B2 | 7/2014 | Shih |
| 8,801,316 B1 | 8/2014 | Abedini |
| D713,538 S | 9/2014 | Van Valen et al. |
| 8,821,483 B2 | 9/2014 | Boutoussov et al. |
| 8,827,990 B2 | 9/2014 | Van Valen et al. |
| 8,834,450 B1 | 9/2014 | McCrary et al. |
| 8,834,457 B2 | 9/2014 | Cao |
| 8,926,323 B2 | 1/2015 | Mossle |
| 8,944,814 B2 | 2/2015 | Mossle |
| 8,977,085 B2 | 3/2015 | Walsh et al. |
| 8,978,930 B2 | 3/2015 | Bublewitz et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,025,625 B2 | 5/2015 | Skrabelj et al. |
| 9,050,157 B2 | 6/2015 | Boyd et al. |
| 9,052,805 B2 | 6/2015 | Boutoussov et al. |
| 9,060,845 B2 | 6/2015 | Van Valen et al. |
| 9,084,651 B2 | 7/2015 | Laufer |
| 9,101,377 B2 | 8/2015 | Boutoussov et al. |
| 9,186,222 B2 | 11/2015 | Marincek et al. |
| D745,966 S | 12/2015 | Piorek et al. |
| 9,204,946 B2 | 12/2015 | Kotlarchik et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 9,408,781 B2 | 8/2016 | Qian et al. |
| 9,492,244 B2 | 11/2016 | Bergheim et al. |
| 9,504,536 B2 | 11/2016 | Bergheim et al. |
| 9,545,295 B2 | 1/2017 | Sung et al. |
| 9,572,632 B2 | 2/2017 | Lukac et al. |
| 9,579,174 B2 | 2/2017 | Yamamoto et al. |
| 9,597,168 B2 | 3/2017 | Black et al. |
| 9,603,676 B1 | 3/2017 | Bochi |
| 9,610,125 B2 | 4/2017 | Kazic et al. |
| 9,675,426 B2 | 6/2017 | Bergheim et al. |
| 9,696,893 B2 | 7/2017 | Boutoussov et al. |
| 9,700,382 B2 | 7/2017 | Pond et al. |
| 9,700,384 B2 | 7/2017 | Yamamoto et al. |
| 9,700,394 B2 | 7/2017 | Yamamoto et al. |
| 9,713,511 B2 | 7/2017 | Lifshitz |
| 9,730,773 B2 | 8/2017 | Uchitel et al. |
| 9,743,999 B2 | 8/2017 | Policicchio |
| 9,788,899 B2 | 10/2017 | Sivriver et al. |
| 9,820,827 B2 | 11/2017 | Feine et al. |
| 9,820,834 B2 | 11/2017 | Maxwell et al. |
| 9,864,485 B2 | 1/2018 | Patton et al. |
| 9,867,997 B2 | 1/2018 | Boutoussov et al. |
| 9,872,748 B2 | 1/2018 | Schoeffel |
| 9,877,801 B2 | 1/2018 | Khakpour et al. |
| D812,231 S | 3/2018 | Duncan et al. |
| D813,391 S | 3/2018 | Duncan et al. |
| 9,931,187 B2 | 4/2018 | Fregoso et al. |
| 9,956,039 B2 | 5/2018 | Boutoussov et al. |
| 9,987,200 B2 | 6/2018 | Kishen |
| 10,010,388 B2 | 7/2018 | Gharib et al. |
| 10,016,263 B2 | 7/2018 | Gharib et al. |
| D824,935 S | 8/2018 | Boutoussov et al. |
| 10,039,625 B2 | 8/2018 | Gharib et al. |
| 10,039,932 B2 | 8/2018 | Van Valen |
| 10,098,708 B2 | 10/2018 | Pond |
| 10,098,717 B2 | 10/2018 | Bergheim et al. |
| 10,130,424 B2 | 11/2018 | Boutoussov et al. |
| 10,314,671 B2 | 6/2019 | Lifshitz et al. |
| 10,321,957 B2 | 6/2019 | Boutoussov et al. |
| 10,327,866 B2 | 6/2019 | Lifshitz et al. |
| 10,335,249 B2 | 7/2019 | Hiemer et al. |
| 10,363,120 B2 | 7/2019 | Khakpour et al. |
| 10,420,629 B2 | 9/2019 | Buchanan |
| 10,420,630 B2 | 9/2019 | Bergheim et al. |
| 10,430,061 B2 | 10/2019 | Boutoussov et al. |
| 10,450,656 B2 | 10/2019 | Sivriver et al. |
| 10,518,299 B2 | 12/2019 | Lukac et al. |
| 10,561,560 B2 | 2/2020 | Boutoussov et al. |
| 10,617,498 B2 | 4/2020 | Gharib et al. |
| 10,631,962 B2 | 4/2020 | Bergheim et al. |
| 10,702,355 B2 | 7/2020 | Bergheim et al. |
| 10,722,325 B2 | 7/2020 | Khakpour et al. |
| 10,729,514 B2 | 8/2020 | Buchanan |
| D896,827 S | 9/2020 | Boutoussov et al. |
| 10,779,908 B2 | 9/2020 | Dresser et al. |
| 10,779,920 B2 | 9/2020 | Buchanan |
| 10,806,543 B2 | 10/2020 | Bergheim et al. |
| 10,806,544 B2 | 10/2020 | Khakpour et al. |
| 10,835,355 B2 | 11/2020 | Gharib et al. |
| 10,877,630 B2 | 12/2020 | Patton et al. |
| D923,038 S | 6/2021 | Boutoussov et al. |
| 11,103,309 B2 | 8/2021 | Boutoussov et al. |
| 11,103,333 B2 | 8/2021 | Khakpour et al. |
| 11,141,249 B2 | 10/2021 | Evans et al. |
| 11,160,455 B2 | 11/2021 | Islam |
| 11,160,645 B2 | 11/2021 | Bergheim et al. |
| 11,173,010 B2 | 11/2021 | Boutoussov et al. |
| 11,173,019 B2 | 11/2021 | Bergheim et al. |
| 11,193,209 B2 | 12/2021 | Sivriver et al. |
| 11,202,687 B2 | 12/2021 | Boutoussov et al. |
| 11,213,375 B2 | 1/2022 | Khakpour et al. |
| 11,250,941 B2 | 2/2022 | Patton et al. |
| 11,284,978 B2 | 3/2022 | Bergheim et al. |
| 11,350,993 B2 | 6/2022 | DiVito et al. |
| 11,426,239 B2 * | 8/2022 | DiVito .................. A61B 18/26 |
| 2001/0041324 A1 | 11/2001 | Riitano |
| 2002/0012897 A1 | 1/2002 | Tingley et al. |
| 2002/0014855 A1 | 2/2002 | Rizoiu et al. |
| 2002/0072032 A1 | 6/2002 | Senn et al. |
| 2002/0086264 A1 | 7/2002 | Okawa et al. |
| 2002/0090594 A1 | 7/2002 | Riitano et al. |
| 2002/0108614 A1 | 8/2002 | Schultz |
| 2002/0142260 A1 | 10/2002 | Pond |
| 2002/0183728 A1 | 12/2002 | Rosenberg et al. |
| 2003/0013063 A1 | 1/2003 | Goldman |
| 2003/0013064 A1 | 1/2003 | Zirkel |
| 2003/0022126 A1 | 1/2003 | Buchalla et al. |
| 2003/0023234 A1 | 1/2003 | Daikuzono |
| 2003/0027100 A1 | 2/2003 | Grant |
| 2003/0096213 A1 | 5/2003 | Hickok et al. |
| 2003/0121532 A1 | 7/2003 | Coughlin et al. |
| 2003/0124485 A1 | 7/2003 | Teraushi |
| 2003/0129560 A1 | 7/2003 | Atkin |
| 2003/0158544 A1 | 8/2003 | Slatkine |
| 2003/0191429 A1 | 10/2003 | Andrew et al. |
| 2003/0207231 A1 | 11/2003 | Nance |
| 2003/0207232 A1 | 11/2003 | Todd et al. |
| 2003/0211083 A1 | 11/2003 | Vogel et al. |
| 2003/0215768 A1 | 11/2003 | Aumuller et al. |
| 2003/0236517 A1 | 12/2003 | Appling |
| 2004/0038170 A1 | 2/2004 | Hiszowicz et al. |
| 2004/0048226 A1 | 3/2004 | Garman |
| 2004/0063073 A1 | 4/2004 | Kajimoto et al. |
| 2004/0063074 A1 | 4/2004 | Fisher |
| 2004/0068256 A1 | 4/2004 | Rizoiu et al. |
| 2004/0072122 A1 | 4/2004 | Hegemann |
| 2004/0073374 A1 | 4/2004 | Lockhart et al. |
| 2004/0092925 A1 | 5/2004 | Rizoiu et al. |
| 2004/0101809 A1 | 5/2004 | Weiss et al. |
| 2004/0102782 A1 | 5/2004 | Vercellotti et al. |
| 2004/0126732 A1 | 7/2004 | Nusstein |
| 2004/0127892 A1 | 7/2004 | Harris |
| 2004/0166473 A1 | 8/2004 | Cohen |
| 2004/0193236 A1 | 9/2004 | Altshuler |
| 2004/0210276 A1 | 10/2004 | Altshuler et al. |
| 2004/0224288 A1 | 11/2004 | Bornstein |
| 2004/0259053 A1 | 12/2004 | Bekov et al. |

(56) References Cited

U.S. PATENT DOCUMENTS

| | | |
|---|---|---|
| 2005/0064371 A1 | 3/2005 | Soukos et al. |
| 2005/0065497 A1 | 3/2005 | Levatino |
| 2005/0096529 A1 | 5/2005 | Cooper et al. |
| 2005/0112525 A1 | 5/2005 | McPherson et al. |
| 2005/0136375 A1 | 6/2005 | Sicurelli, Jr. et al. |
| 2005/0142517 A1 | 6/2005 | Frysh et al. |
| 2005/0155622 A1 | 7/2005 | Leis |
| 2005/0170312 A1 | 8/2005 | Pond |
| 2005/0175960 A1 | 8/2005 | Wiek et al. |
| 2005/0186530 A1 | 8/2005 | Eagle |
| 2005/0199261 A1 | 9/2005 | Vanhauwemeiren et al. |
| 2005/0256517 A1 | 11/2005 | Boutoussov |
| 2005/0271531 A1 | 12/2005 | Brown, Jr. et al. |
| 2005/0277898 A1 | 12/2005 | Dimalanta et al. |
| 2005/0281530 A1 | 12/2005 | Rizoiu et al. |
| 2005/0281887 A1 | 12/2005 | Rizoiu |
| 2005/0283143 A1 | 12/2005 | Rizoiu |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0110710 A1 | 5/2006 | Schemmer et al. |
| 2006/0142743 A1 | 6/2006 | Rizoiu et al. |
| 2006/0142744 A1 | 6/2006 | Boutoussov |
| 2006/0142745 A1 | 6/2006 | Boutoussov |
| 2006/0184071 A1 | 8/2006 | Klopotek |
| 2006/0189965 A1 | 8/2006 | Litvak et al. |
| 2006/0227653 A1 | 10/2006 | Keller |
| 2006/0234182 A1 | 10/2006 | Ruddle et al. |
| 2006/0234183 A1 | 10/2006 | Ruddle et al. |
| 2006/0240381 A1 | 10/2006 | Rizoiu et al. |
| 2006/0240386 A1 | 10/2006 | Yaniv et al. |
| 2006/0241574 A1 | 10/2006 | Rizoiu |
| 2006/0246395 A1 | 11/2006 | Pond |
| 2006/0257819 A1 | 11/2006 | Johnson |
| 2006/0264808 A1 | 11/2006 | Staid et al. |
| 2007/0003604 A1 | 1/2007 | Jones |
| 2007/0009449 A1 | 1/2007 | Kanca |
| 2007/0014517 A1 | 1/2007 | Rizoiu et al. |
| 2007/0016176 A1 | 1/2007 | Boutoussov et al. |
| 2007/0016177 A1 | 1/2007 | Vaynberg et al. |
| 2007/0016178 A1 | 1/2007 | Vaynberg et al. |
| 2007/0020576 A1 | 1/2007 | Osborn et al. |
| 2007/0042315 A1 | 2/2007 | Boutoussov et al. |
| 2007/0042316 A1 | 2/2007 | Pichat et al. |
| 2007/0049911 A1 | 3/2007 | Brown |
| 2007/0054233 A1 | 3/2007 | Rizoiu et al. |
| 2007/0054235 A1 | 3/2007 | Rizoiu et al. |
| 2007/0054236 A1 | 3/2007 | Rizoiu et al. |
| 2007/0059660 A1 | 3/2007 | Rizoiu et al. |
| 2007/0060917 A1 | 3/2007 | Andriasyan |
| 2007/0072153 A1 | 3/2007 | Gross et al. |
| 2007/0083120 A1 | 4/2007 | Cain et al. |
| 2007/0088295 A1 | 4/2007 | Bankiewicz |
| 2007/0099149 A1 | 5/2007 | Levy et al. |
| 2007/0104419 A1 | 5/2007 | Rizoiu et al. |
| 2007/0128576 A1 | 6/2007 | Boutoussov |
| 2007/0135797 A1 | 6/2007 | Hood et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0184402 A1 | 8/2007 | Boutoussov et al. |
| 2007/0190482 A1 | 8/2007 | Rizoiu |
| 2007/0208328 A1 | 9/2007 | Boutoussov et al. |
| 2007/0224575 A1 | 9/2007 | Dieras et al. |
| 2007/0265605 A1 | 11/2007 | Vaynberg et al. |
| 2007/0287125 A1 | 12/2007 | Weill |
| 2007/0298369 A1 | 12/2007 | Rizoiu et al. |
| 2008/0014545 A1 | 1/2008 | Schippers |
| 2008/0032259 A1 | 2/2008 | Schoeffel |
| 2008/0033411 A1 | 2/2008 | Manvel Artyom et al. |
| 2008/0044789 A1 | 2/2008 | Johnson |
| 2008/0065057 A1 | 3/2008 | Andriasyan |
| 2008/0070185 A1 | 3/2008 | Rizoiu et al. |
| 2008/0070195 A1 | 3/2008 | DiVito et al. |
| 2008/0085490 A1 | 4/2008 | Jabri |
| 2008/0097417 A1 | 4/2008 | Jones et al. |
| 2008/0102416 A1 | 5/2008 | Karazivan et al. |
| 2008/0125677 A1 | 5/2008 | Van Valen |
| 2008/0138761 A1 | 6/2008 | Pond |
| 2008/0138764 A1 | 6/2008 | Rizoiu |
| 2008/0138772 A1 | 6/2008 | Bornstein |
| 2008/0151953 A1 | 6/2008 | Rizoiu et al. |
| 2008/0155770 A1 | 7/2008 | Grez |
| 2008/0157690 A1 | 7/2008 | Rizoiu et al. |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0160481 A1 | 7/2008 | Schoeffel |
| 2008/0188848 A1 | 8/2008 | Deutmeyer et al. |
| 2008/0199831 A1 | 8/2008 | Teichert et al. |
| 2008/0209650 A1 | 9/2008 | Brewer et al. |
| 2008/0219629 A1 | 9/2008 | Rizoiu et al. |
| 2008/0221558 A1 | 9/2008 | Becker |
| 2008/0255498 A1 | 10/2008 | Houle |
| 2008/0274438 A1 | 11/2008 | Schemmer |
| 2008/0276192 A1 | 11/2008 | Jones et al. |
| 2008/0285600 A1 | 11/2008 | Marincek et al. |
| 2008/0311045 A1 | 12/2008 | Hardy |
| 2008/0311540 A1 | 12/2008 | Gottenbos et al. |
| 2008/0314199 A1 | 12/2008 | Niemi et al. |
| 2009/0004621 A1 | 1/2009 | Quan et al. |
| 2009/0011380 A1 | 1/2009 | Wang |
| 2009/0031515 A1 | 2/2009 | Rizoiu et al. |
| 2009/0035717 A1 | 2/2009 | Rizoiu et al. |
| 2009/0042171 A1 | 2/2009 | Rizoiu et al. |
| 2009/0047624 A1 | 2/2009 | Tsai |
| 2009/0047634 A1 | 2/2009 | Calvert |
| 2009/0054881 A1 | 2/2009 | Krespi |
| 2009/0059994 A1 | 3/2009 | Nemes et al. |
| 2009/0067189 A1 | 3/2009 | Boutoussov et al. |
| 2009/0092947 A1* | 4/2009 | Cao .................. A61K 45/06 433/215 |
| 2009/0105597 A1 | 4/2009 | Abraham |
| 2009/0105707 A1 | 4/2009 | Rizoiu et al. |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0143775 A1 | 6/2009 | Rizoiu et al. |
| 2009/0170052 A1 | 7/2009 | Borczyk |
| 2009/0208898 A1 | 8/2009 | Kaplan |
| 2009/0211042 A1 | 8/2009 | Bock |
| 2009/0225060 A1 | 9/2009 | Rizoiu et al. |
| 2009/0227185 A1 | 9/2009 | Summers et al. |
| 2009/0263759 A1 | 10/2009 | Van Herpern |
| 2009/0275935 A1 | 11/2009 | McKee |
| 2009/0281531 A1 | 11/2009 | Rizoiu et al. |
| 2009/0298004 A1 | 12/2009 | Rizoiu |
| 2010/0015576 A1 | 1/2010 | Altshuler et al. |
| 2010/0042040 A1 | 2/2010 | Arentz |
| 2010/0047734 A1 | 2/2010 | Harris et al. |
| 2010/0068679 A1 | 3/2010 | Zappini |
| 2010/0086892 A1 | 4/2010 | Riozoui et al. |
| 2010/0092922 A1 | 4/2010 | Ruddle |
| 2010/0125291 A1 | 5/2010 | Rizoiu et al. |
| 2010/0143861 A1 | 6/2010 | Gharib |
| 2010/0151406 A1 | 6/2010 | Boutoussov et al. |
| 2010/0151407 A1 | 6/2010 | Rizoiu et al. |
| 2010/0152634 A1 | 6/2010 | Dove |
| 2010/0160838 A1 | 6/2010 | Krespi |
| 2010/0160904 A1 | 6/2010 | McMillan et al. |
| 2010/0167226 A1 | 7/2010 | Altshuler et al. |
| 2010/0167228 A1 | 7/2010 | Rizoiu et al. |
| 2010/0185188 A1 | 7/2010 | Boutoussov et al. |
| 2010/0190133 A1 | 7/2010 | Martinez |
| 2010/0206324 A1 | 8/2010 | Paschke |
| 2010/0209867 A1 | 8/2010 | Becker et al. |
| 2010/0229316 A1 | 9/2010 | Hohlbein et al. |
| 2010/0233645 A1 | 9/2010 | Rizoiu |
| 2010/0233649 A1 | 9/2010 | McPeek et al. |
| 2010/0261136 A1 | 10/2010 | Schulte et al. |
| 2010/0272764 A1 | 10/2010 | Latta et al. |
| 2010/0273125 A1 | 10/2010 | Janssen et al. |
| 2010/0279250 A1 | 11/2010 | Pond et al. |

(56) References Cited

U.S. PATENT DOCUMENTS

| | | |
|---|---|---|
| 2010/0279251 A1 | 11/2010 | Pond |
| 2010/0330539 A1 | 12/2010 | Glover et al. |
| 2011/0020765 A1 | 1/2011 | Maxwell et al. |
| 2011/0027746 A1 | 2/2011 | McDonough et al. |
| 2011/0027747 A1 | 2/2011 | Fougere et al. |
| 2011/0070552 A1 | 3/2011 | Bornstein |
| 2011/0072605 A1 | 3/2011 | Steur |
| 2011/0076638 A1 | 3/2011 | Gottenbos et al. |
| 2011/0087605 A1 | 4/2011 | Pond |
| 2011/0096549 A1 | 4/2011 | Boutoussov et al. |
| 2011/0111365 A1 | 5/2011 | Gharib et al. |
| 2011/0129789 A1 | 6/2011 | Rizoiu et al. |
| 2011/0136935 A1 | 6/2011 | Khor et al. |
| 2011/0143310 A1 | 6/2011 | Hunter |
| 2011/0151394 A1 | 6/2011 | Rizoiu et al. |
| 2011/0183284 A1 | 7/2011 | Yamanaka et al. |
| 2011/0189627 A1 | 8/2011 | Gharib et al. |
| 2011/0189630 A1 | 8/2011 | Koubi |
| 2011/0198370 A1 | 8/2011 | Ho |
| 2011/0200959 A1 | 8/2011 | Rizoiu et al. |
| 2011/0217665 A1 | 9/2011 | Walsh et al. |
| 2011/0229845 A1 | 9/2011 | Chen |
| 2011/0256503 A1 | 10/2011 | Fraser |
| 2011/0269099 A1 | 11/2011 | Glover et al. |
| 2011/0270241 A1 | 11/2011 | Boutoussov |
| 2011/0281230 A1 | 11/2011 | Rizoiu et al. |
| 2011/0281231 A1 | 11/2011 | Rizoiu et al. |
| 2012/0065711 A1 | 3/2012 | Netchitailo et al. |
| 2012/0077144 A1 | 3/2012 | Fougere et al. |
| 2012/0094251 A1 | 4/2012 | MÖssle |
| 2012/0099815 A1 | 4/2012 | Boutoussov et al. |
| 2012/0135368 A1 | 5/2012 | Rizoiu et al. |
| 2012/0135373 A1 | 5/2012 | Cheng et al. |
| 2012/0141953 A1 | 6/2012 | Mueller |
| 2012/0148979 A1 | 6/2012 | Ruddle |
| 2012/0240647 A1 | 9/2012 | Montemurro |
| 2012/0276497 A1 | 11/2012 | Gharib |
| 2012/0282566 A1 | 11/2012 | Rizoiu et al. |
| 2012/0282570 A1 | 11/2012 | Mueller |
| 2012/0021375 A1 | 12/2012 | Binner et al. |
| 2013/0040267 A1 | 2/2013 | Bergheim |
| 2013/0066324 A1 | 3/2013 | Engqvist et al. |
| 2013/0084544 A1 | 4/2013 | Boutoussov et al. |
| 2013/0084545 A1 | 4/2013 | Netchitailo et al. |
| 2013/0085485 A1 | 4/2013 | Van Valen et al. |
| 2013/0085486 A1 | 4/2013 | Boutoussov et al. |
| 2013/0086758 A1 | 4/2013 | Boutoussov et al. |
| 2013/0089829 A1 | 4/2013 | Boutoussov et al. |
| 2013/0110101 A1 | 5/2013 | Van Valen et al. |
| 2013/0115568 A1 | 5/2013 | Jelovac et al. |
| 2013/0131656 A1 | 5/2013 | Marincek et al. |
| 2013/0143180 A1 | 6/2013 | Glover et al. |
| 2013/0177865 A1* | 7/2013 | Ostler ............... A61C 1/0046 433/29 |
| 2013/0178847 A1 | 7/2013 | Rizoiu et al. |
| 2013/0190738 A1 | 7/2013 | Lukac et al. |
| 2013/0190743 A1 | 7/2013 | Boutoussov et al. |
| 2013/0216980 A1 | 8/2013 | Boronkay et al. |
| 2013/0236857 A1 | 9/2013 | Boutoussov et al. |
| 2013/0273494 A1 | 10/2013 | Boutoussov et al. |
| 2013/0274724 A1 | 10/2013 | Rizoiu |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0080090 A1 | 3/2014 | Laufer |
| 2014/0087333 A1 | 3/2014 | DiVito et al. |
| 2014/0113243 A1 | 4/2014 | Boutoussov et al. |
| 2014/0124969 A1 | 5/2014 | Blaisdell et al. |
| 2014/0127641 A1 | 5/2014 | Hilscher et al. |
| 2014/0147804 A1 | 5/2014 | Yamamoto et al. |
| 2014/0170588 A1 | 6/2014 | Miller et al. |
| 2014/0205965 A1 | 7/2014 | Boutoussov et al. |
| 2014/0220511 A1 | 8/2014 | DiVito et al. |
| 2014/0242551 A1 | 8/2014 | Downs |
| 2014/0257254 A1 | 9/2014 | Boutoussov et al. |
| 2014/0261534 A1 | 9/2014 | Schepis |
| 2014/0272782 A1 | 9/2014 | Luettgen et al. |
| 2014/0303692 A1 | 10/2014 | Pignatelli et al. |
| 2014/0342303 A1 | 11/2014 | Altshuler et al. |
| 2014/0349246 A1 | 11/2014 | Johnson et al. |
| 2015/0010878 A1 | 1/2015 | Seibel et al. |
| 2015/0017599 A1 | 1/2015 | Marincek et al. |
| 2015/0017607 A1 | 1/2015 | Nelson et al. |
| 2015/0030991 A1 | 1/2015 | Sung et al. |
| 2015/0044630 A1 | 2/2015 | Gharib et al. |
| 2015/0056567 A1 | 2/2015 | Fregoso et al. |
| 2015/0056570 A1 | 2/2015 | Kansal |
| 2015/0126984 A1 | 5/2015 | Boutoussov et al. |
| 2015/0147715 A1 | 5/2015 | Breysse |
| 2015/0147717 A1 | 5/2015 | Taylor et al. |
| 2015/0150650 A1 | 6/2015 | Netchitailo et al. |
| 2015/0173850 A1 | 6/2015 | Garrigues et al. |
| 2015/0182283 A1 | 7/2015 | Boutoussov et al. |
| 2015/0190597 A1 | 7/2015 | Zachar et al. |
| 2015/0216398 A1 | 8/2015 | Yang et al. |
| 2015/0216597 A1 | 8/2015 | Boutoussov et al. |
| 2015/0216622 A1 | 8/2015 | Vartanian et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0342679 A1 | 12/2015 | Boutoussov et al. |
| 2015/0359672 A1 | 12/2015 | Van Valen et al. |
| 2015/0367142 A1 | 12/2015 | Kazic et al. |
| 2015/0374471 A1 | 12/2015 | Stangel et al. |
| 2016/0022392 A1 | 1/2016 | Chang et al. |
| 2016/0067149 A1 | 3/2016 | Kishen |
| 2016/0100921 A1 | 4/2016 | Ungar |
| 2016/0113733 A1 | 4/2016 | Pond et al. |
| 2016/0113745 A1 | 4/2016 | Golub et al. |
| 2016/0128815 A1 | 5/2016 | Birdee et al. |
| 2016/0135581 A1 | 5/2016 | Pai |
| 2016/0149370 A1 | 5/2016 | Marincek et al. |
| 2016/0149372 A1 | 5/2016 | Marincek et al. |
| 2016/0220200 A1 | 8/2016 | Sandholm et al. |
| 2016/0270889 A1 | 9/2016 | Casabonne et al. |
| 2016/0334283 A1 | 11/2016 | Scurtescu et al. |
| 2017/0027646 A1 | 2/2017 | DivVito et al. |
| 2017/0027647 A1 | 2/2017 | DiVito et al. |
| 2017/0036253 A1 | 2/2017 | Lukac et al. |
| 2017/0056143 A1 | 3/2017 | Hyun |
| 2017/0189149 A1 | 7/2017 | Golub et al. |
| 2017/0196658 A1 | 7/2017 | Schoeffel |
| 2017/0197071 A1 | 7/2017 | Gottenbos |
| 2017/0216579 A1 | 8/2017 | Becker et al. |
| 2017/0265965 A1 | 9/2017 | Chow et al. |
| 2017/0274220 A1 | 9/2017 | Ertl et al. |
| 2017/0281305 A1 | 10/2017 | Bergheim |
| 2017/0300220 A1 | 10/2017 | Boutoussov et al. |
| 2017/0325889 A1 | 11/2017 | DiVito et al. |
| 2017/0340523 A1 | 11/2017 | Guzman |
| 2018/0008347 A9 | 1/2018 | DeVito et al. |
| 2018/0021104 A1 | 1/2018 | Duncan et al. |
| 2018/0104020 A1 | 4/2018 | Boutoussov et al. |
| 2018/0125608 A1 | 5/2018 | Gottenbos et al. |
| 2018/0140865 A1 | 5/2018 | Boutoussov et al. |
| 2018/0214247 A1 | 8/2018 | Sharma et al. |
| 2018/0228581 A1 | 8/2018 | Ouyang |
| 2018/0228582 A1 | 8/2018 | Shin |
| 2018/0257962 A1 | 9/2018 | Montemurro |
| 2018/0360563 A1 | 12/2018 | Khakpour |
| 2019/0059996 A1 | 2/2019 | Duncan et al. |
| 2019/0117078 A1 | 4/2019 | Sharma et al. |
| 2019/0142516 A1 | 5/2019 | Boutoussov et al. |
| 2019/0175401 A1 | 6/2019 | Van Valen et al. |
| 2019/0282332 A1 | 9/2019 | Lifshitz et al. |
| 2019/0282347 A1 | 9/2019 | Gharib et al. |
| 2019/0336219 A9 | 11/2019 | DiVito |
| 2020/0069402 A1 | 3/2020 | Gharib |

(56) References Cited

U.S. PATENT DOCUMENTS

| | | | |
|---|---|---|---|
| 2020/0085534 A1 | 3/2020 | Kim et al. |
| 2020/0139146 A1 | 5/2020 | Khakpour |
| 2020/0179209 A1 | 6/2020 | Boutoussov et al. |
| 2020/0197143 A1 | 6/2020 | Snyder et al. |
| 2020/0205934 A1 | 7/2020 | Groves, Jr. et al. |
| 2020/0253369 A1 | 8/2020 | De Gentile et al. |
| 2020/0253702 A1 | 8/2020 | De Gentile et al. |
| 2020/0254586 A1 | 8/2020 | Sanders et al. |
| 2020/0268491 A1 | 8/2020 | Shotton et al. |
| 2020/0281688 A1 | 9/2020 | Lares et al. |
| 2020/0297455 A1 | 9/2020 | Bergheim |
| 2020/0330184 A1 | 10/2020 | Boutoussov et al. |
| 2020/0347191 A1 | 11/2020 | Gomurashvili |
| 2020/0360108 A1 | 11/2020 | Gomurashvili et al. |
| 2021/0038344 A1 | 2/2021 | Khakpour |
| 2021/0068921 A1 | 3/2021 | Bergheim |
| 2021/0069756 A1 | 3/2021 | Lukac et al. |
| 2021/0077234 A1 | 3/2021 | Gharib et al. |
| 2021/0082562 A1 | 3/2021 | Patton et al. |
| 2021/0085435 A1 | 3/2021 | Bergheim |
| 2021/0106402 A1 | 4/2021 | Khakpour et al. |
| 2021/0121275 A1 | 4/2021 | Parham et al. |
| 2021/0145538 A1 | 5/2021 | Boutoussov et al. |
| 2021/0153937 A1 | 5/2021 | Duncan et al. |
| 2021/0186824 A1 | 6/2021 | Gomurashvili et al. |
| 2021/0386532 A1 | 12/2021 | Khakpour et al. |
| 2022/0015829 A1 | 1/2022 | Boutoussov et al. |
| 2022/0022961 A1 | 1/2022 | Boutoussov et al. |
| 2022/0031548 A1 | 2/2022 | Boutoussov et al. |
| 2022/0054230 A1 | 2/2022 | Lifshitz et al. |
| 2022/0071735 A1 | 3/2022 | Boutoussov et al. |
| 2022/0186376 A1 | 6/2022 | Sivriver et al. |
| 2022/0202525 A1 | 6/2022 | Boutoussov et al. |
| 2022/0208334 A1 | 6/2022 | Patton et al. |
| 2022/0233291 A1 | 7/2022 | DeZan et al. |
| 2022/0296346 A1 | 9/2022 | Bergheim et al. |
| 2022/0313405 A1 | 10/2022 | Bergheim et al. |
| 2022/0370177 A1 | 11/2022 | Khakpour et al. |

FOREIGN PATENT DOCUMENTS

| | | |
|---|---|---|
| CN | 2189448 Y | 2/1995 |
| CN | 1127982 | 7/1996 |
| CN | 2693189 Y | 4/2005 |
| CN | 2936192 Y | 8/2007 |
| CN | 200953143 | 10/2007 |
| CN | 201070397 Y | 6/2008 |
| CN | 201370644 Y | 12/2009 |
| CN | 101632849 A | 1/2010 |
| CN | 103027762 A | 4/2013 |
| CN | 107080697 A | 8/2017 |
| DE | 3708801 | 9/1988 |
| DE | 4404983 | 9/1994 |
| DE | 10248336 | 5/2004 |
| DE | 102005028925 | 1/2007 |
| EP | 0261466 | 3/1988 |
| EP | 0436316 | 7/1991 |
| EP | 0685454 | 12/1995 |
| EP | 0830852 | 3/1998 |
| EP | 0902654 | 8/2004 |
| FR | 1225547 | 7/1960 |
| FR | 2831050 | 4/2003 |
| GB | 917633 | 2/1963 |
| GB | 2011305 | 7/1979 |
| JP | 51-064791 A | 4/1976 |
| JP | 01-313048 | 12/1989 |
| JP | 05-169039 A | 9/1993 |
| JP | H07-155335 | 6/1995 |
| JP | H08-117335 A | 5/1996 |
| JP | H08-1118 A | 9/1996 |
| JP | 09-84809 A | 3/1997 |
| JP | 09-276292 | 10/1997 |
| JP | 10-33548 | 2/1998 |
| JP | H11-28219 A | 2/1999 |
| JP | 11-113927 A | 4/1999 |
| JP | H11-504843 | 5/1999 |
| JP | 11-244303 A | 9/1999 |
| JP | 2000-254153 A | 9/2000 |
| JP | 2002-209911 | 7/2002 |
| JP | 2004-313659 | 11/2003 |
| JP | 3535685 B2 | 6/2004 |
| JP | 2004-261288 | 9/2004 |
| JP | 2005-052754 | 3/2005 |
| JP | 2005-080802 | 3/2005 |
| JP | 2005-095374 | 4/2005 |
| JP | 2006-247619 | 9/2006 |
| JP | 2008-93080 | 4/2008 |
| JP | 2008-132099 | 6/2008 |
| JP | 2009-114953 | 5/2009 |
| JP | 2010-247133 | 11/2010 |
| KR | 10-2008-0105713 A | 12/2008 |
| KR | 10-2012-0084897 A | 7/2012 |
| KR | 10-2013-0022553 A | 3/2013 |
| KR | 10-2013-0141103 A | 12/2013 |
| KR | 2004-72508 Y1 | 5/2014 |
| RU | 2326611 C1 | 12/2011 |
| TW | M 336 027 U | 7/2008 |
| WO | WO 1992/004871 | 4/1992 |
| WO | WO 1992/012685 | 8/1992 |
| WO | WO 1995/035069 | 12/1995 |
| WO | WO 1997/021420 | 6/1997 |
| WO | WO 1998/023219 | 6/1998 |
| WO | WO 1998/025536 | 6/1998 |
| WO | WO 1999/63904 | 12/1999 |
| WO | WO 2000/045731 | 8/2000 |
| WO | WO 2000/074587 | 12/2000 |
| WO | WO 2001/026577 | 4/2001 |
| WO | WO 2001/26735 | 4/2001 |
| WO | WO 2001/93773 | 12/2001 |
| WO | WO 2002/078644 | 10/2002 |
| WO | WO 2003/086223 | 10/2003 |
| WO | WO 2004/032881 | 4/2004 |
| WO | WO 2006/082101 | 8/2006 |
| WO | WO 2008/120018 | 10/2008 |
| WO | WO 2011/114718 | 9/2011 |
| WO | WO 2012/074918 | 6/2012 |
| WO | WO 2013/15700 | 1/2013 |
| WO | WO 2013/057519 | 4/2013 |
| WO | WO 2013/061251 | 5/2013 |
| WO | WO 2013/160888 | 10/2013 |
| WO | WO 2022/099258 | 5/2022 |

OTHER PUBLICATIONS

U.S. Appl. No. 17/452,731, filed Oct. 28, 2021, Bergheim et al.
U.S. Appl. No. 17/454,725, filed Nov. 12, 2021, Bergeim et al.
U.S. Appl. No. 17/562,798, filed Dec. 27, 2021, Khakpour et al.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
ADA American Dental Association, "Glossary of Dental Clinical and Administrative Terms," http://www.ada.org/en/publications/cdt/glossary-of-dental-clinical-and-administrative-ter, downloaded May 4, 2017, in 46 pages.
Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.
Ahmad et al., "Ultrasonic Debridement of Root Canals: Acoustic Cavitation and Its Relevance," Journal of Endontics, vol. 14, No. 10, pp. 486-493, Oct. 1988.
Al-Jadaa et al; Acoustic Hypochlorite Activation in Simulated Curved Canals; pp. 1408-1411; Journal of Endodontics, vol. 35, No. 10; Oct. 2009.
Alomairy, Evaluating two techniques on removal of fractured rotary nickel-titanium endodontic instruments from root canals: an in vitro study. J Endod 2009;35:559-62.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.

(56) References Cited

OTHER PUBLICATIONS

Anantharamaiah et al; A simple expression for predicting the inlet roundness of micro-nozzles; pp. N31-N39; Journal of Micromechanics and Microengineering, vol. 17; Mar. 21, 2007.

Anantharamaiah et al; A study on flow through hydroentangling nozzles and their degradation; pp. 4582-4594; Chemical Engineering Science, vol. 61; May 2006.

Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.

Attin et al; Clinical evaluation of the cleansing properties of the nonistrumental technique for cleaning root canals; pp. 929-933; International Endodontic Journal, vol. 35, Issue 11; Nov. 2002.

Aydin, et al., "Fracture resistance of root-filled teeth after cavity preparation with conventional burs, Er:YAG and Er,Cr:YSGG Lasers," Eur Oral Res 2018; 52: 59-63.

Bader et al., "Indications and limitations of Er:YAG laser applications in dentistry," archive ouverte UNIGE, http://archive-ouverte.unige.ch. American Journal of Denistry, 2006, vol. 19, No. 3, p. 178-186.

Bahia, et al.: Physical and mechanical characterization and the influence of cyclic loading on the behaviour of nickel-titanium wires employed in the manufacture of rotary endodontic instruments. Int Endod. J. 2005;38:795-801.

Batchelor et al; Analysis of the stability of axisymmetric jets; pp. 529-551; Journal of Fluid Mechanics, vol. 14; Dec. 1962.

Begenir et al; Effect of Nozzle Geometry on Hydroentangling Water Jets: Experimental Observations; pp. 178-184; Textile Research Journal, vol. 74; Feb. 2004.

Begenir, Asli; The Role of Orifice Design in Hydroentanglement; Thesis submitted to North Carolina State University; dated Dec. 2002, in 107 pages.

Biolase Study, Efficacy of the Er,Cr:YSGG laser in the Laser Assisted Endodontic Treatment, Blind Randomized Clinical Trial, in 332 pages, Apr. 11, 2014. URL: https://repositorio-aberto.up.pt/handle/10216/82757.

Borkent et al; Is there gas entrapped on submerged silicon wafers? Visualizing nano-scale bubbles with cavitation; pp. 225-228; Solid State Phenomena, vol. 134 (2008); available online Nov. 2007.

Bornstein, Eric. "Proper use of Er: YAG lasers and contact sapphire tips when cutting teeth and bone: scientific principles and clinical application." Dentistry today 23.8 (2004): 84-89.

Bremond et al; Cavitation on surfaces; pp. S3603-S3608; Journal of Physics: Condensed Matter, vol. 17; Oct. 28, 2005.

Brennen, Christopher E.; Fission of collapsing cavitation bubbles; pp. 153-166; Journal of Fluid Mechanics, vol. 472; Dec. 2002.

Buchanan, "Closed-System Negative Pressure Irrigation: A Serious Inflection Point inRoot Canal Cleaning," Apr. 1, 2020. https://www.dentistrytoday.com/articles/10666.

Chang et al; Effects of Inlet Surface Roughness, Texture, and Nozzle Material on Cavitation; pp. 299-317; Atomization and Sprays, vol. 16 (2006).

Charara, et al.: "Assessment of apical extrusion during root canal procedure with the novel GentleWave system in a simulated apical environment," J Endod 2015. In Press.

Christo, Jonathan Dr., "Efficacy of Sodium Hypochlorite and Er,Cr:YSGG Laser Energised Irrigation Against an Enterococcus faecalis Biofilm", Sep. 2012.

Crump et al., "Relationship of broken root canal instruments to endodontic case prognosis: a clinical investigation," J Am Dent Assoc 1970;80:1341-7.

Culjat et al., "B-Scan Imaging of Human Teeth Using Ultrasound," Apr. 2003, in 4 pages.

D'Arcangelo, et al.: "Broken instrument removal—two cases," J Endod 2000;26:368-70.

De Groot, et al., "Laser-activated irrigation within root canals: cleaning efficacy and flow visualization," Int Endod J. 2009;42:1077-83.

Didenkulov et al.; Nonlinear Acoustic Diagnostics of Scatterer Spatial Distribution in a Cavitation Jet; Nov. 19-23, 2001, pp. 276-278, XI Session of the Russion Acoustical Society.

DiVito et al.: "Cleaning and debriding efficacy of new radial and stripped tips using an Erbium laser on human root canal dentin walls—an in vitro study: SEM observations," undated.

DiVito et al., "The Photoacoustic Efficacy of an Er:YAG Laser with Radial and Stripped Tips on Root Canal Dentin Walls: An SEM Evaluation," J Laser Dent 2011;19(1):156-161.

Dumouchel, Christophe; On the experimental investigation on primary atomization of liquid streams; pp. 371-422; Experimental Fluids, vol. 45; Jun. 22, 2008.

Ebihara et al.: "Er:YAG laser modification of root canal dentine: Influence of pulse duration, repetitive irradiation and water spray," Lasers in Medical Science, 17(3), 198-207, Aug. 2002.

Eddingfield et al; Mathematical Modeling of High Velocity Water Jets; pp. 25-39; Proceedings of 1st U.S. Water Jet Conference; 1981.

El-Din, et al., "Antibacterial Effect of Er,Cr:YSGG Laser Under Various Irradiation Conditions in Root Canals Contaminated With Enterococcus Faecalis," Alexandria Dental Journal. (2017) vol. 42 pp. 108-112.

EMS Electro Medical Systems, "Cleaning", in 2 pages, dated 2005, downloaded from http://www.ems-dent.com/en/endodontics cleaning. htm.

Esen, et al.: "Apical microleakage of root-end cavities prepared by CO2 laser," J Endod 2004;30:662-4.

ESI Endo Soft Instruments, EMS Electro Medical Systems, Brochure in 2 pages, downloaded from www.emsdent.com, dated Jan. 2004.

Feldman, et al.: "Retrieving broken endodontic instruments," J Am Dent Assoc. 1974:88:588-91.

Feng et al; Enhancement of ultrasonic cavitation yield by multi-frequency sonication; pp. 231-236; Ultrasonics Sonochemistry, vol. 9; Oct. 2002.

Flint, E. B., et al., "The Temperature of Cavitation", Science, vol. 253, Sep. 20, 1991, pp. 1397-1399.

Foldyna et al; Acoustic wave propagation in high-pressure system; pp. e1457-e1460; Ultrasonics vol. 44 (Supplement 1); Jun. 8, 2006.

Fors, et al.: "A method for the removal of broken endodontic instruments from root canals," J Endod 1983;9:156-9.

Fuchs, "Ultrasonic Cleaning: Fundamental Theory and Application," Blackstone—Ney Ultrasonics, Jamestown, NY, May 2002.

G.E. Reisman and C.E. Brennen, "Pressure Pulses Generated by Cloud Cavitation", FED—vol. 236, 1996 Fluids Engineering Division Conference, vol. 1, pp. 319-328, ASME 1996.

G.E. Reisman, Y.-C. Wang and C.E. Brennen, "Observations of shock waves in cloud cavitation", J. Fluid Mech. (1998), vol. 355, pp. 255-283.

Gencoglu, et al.: Comparison of the different techniques to remove fractured endodontic instruments from root canal systems. Eur J Dent 2009;3:90-5.

George, M.D.Sc., Ph.D, et al., "Thermal Effects from Modified Endodontic Laser Tips Used in the Apical Third of Root Canals with Erbium-Doped Yttrium Aluminium Garnet and Erbium, Chromium-Doped Yttrium Scandium Gallium Garnet Lasers," Photomedicine and Laser Surgery vol. 28, No. 2, 2010, Mary Ann Liebert, Inc., pp. 161-165.

Ghassemieh et al; Effect of Nozzle Geometry on the Flow Characteristics of Hydroentangling Jets; pp. 444-450; Textile Research Journal, vol. 73; May 2003.

Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.

Gordon, DMD, et al., "The antimicrobial efficacy of the erbium, chromiumyttrium-scandium-gallium-garnet laser with radial emitting tips on root canal dentin walls infected with Enterococcus faecalis," Research—Advances in Dental Products, JADA, vol. 138, Jul. 2007. RFT endolase, Root Calan Therapy System for the Waterlase MD YSGG Laser, Peer-Reviewed Clincal Articles.

Gregorcic, Peter, Matija Jezersek, and Janez Mozina. "Optodynamic energy-conversion efficiency during an Er: YAG-laser-pulse deliv-

(56) References Cited

OTHER PUBLICATIONS ery into a liquid through different fiber-tip geometries." Journal of biomedical optics 17.7 (2012): 075006.
Guidotti R, et al, "Er:YAG 2,940-nm laser fiber in endodontic treatment: a help in removing smear layer," Lasers Med Sci. 2014;29:69-75.
Haapasalo, et al.: "Tissue dissolution by a novel multisonic ultracleaning system and sodium hypochlorite," J Endod 2014;40:1178-81.
Hahn et al; Acoustic resonances in the bubble plume formed by a plunging waterjet; pp. 1751-1782; Proceedings of the Royal Society of London A, vol. 459; May 16, 2003.
Haikel, et al.: Dynamic and cyclic fatigue of engine-driven rotary nickel-titanium endodontic instruments. J Endod 1999;25:434-40.
Haikel, et al.: Dynamic fracture of hybrid endodontic hand instruments compared with traditional files. J Endod 1991;17:217-20.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hulsmann, et al.: Influence of several factors on the success or failure of removal of fractured instruments from the root canal. Endod Dent Traumatol 199;15:252-8.
Hulsmann: "Methods for removing metal obstructions from the root canal," Endod Dent Traumatol 1993;9:223-37.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
Iqbal, et al.: "A comparison of three methods for preparing centered platforms around separated instruments in curved canals," J Endod 2006; 32:48-51.
JLAD, Fall 2015, Issue 3.
Jackson et al; Nozzle Design for Coherent Water Jet Production; pp. 53-89; Proceeding of the 2nd US Water Jet Conference; May 1983.
Jiang, et al., "Evaluation of A Sonic Device Designed to Activate Irrigant in the Root Canal," Journal of endodontics, 36(1): 143-146, Jan. 2010.
Jonathan, et al., "Comparative Evaluation of the Antibacterial Efficacy of Four Different Disinfection Techniques in Minimally Instrumented Experimentally Infected Root Canals: An in vitro Study," International Journal of Laser Densitry, May-Aug. 2013; 3(2): 49-54.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; In CAV2001: Fourth International Symposium on Caviation; California Institute of Technology, Pasadena, CA; dated Jun. 2001.
Kimura et al., "Lasers in endodontics: a review," International Endodontic Journal, 33, 173-185, 2000.
Koch et al., "Irrigant flow during photon-induced photoacoustic streaming (PIPS) using Particle Image Velocimetry (PIV)", Clin. Oral Invest. vol. 20:381-386 (2016).
Kolnick, Justin. "Managing Refractory Endodontic Disease With Radial Apical Cleansing (Report Of Two Clinical Cases)." (Sep. 2018).
Kourti, E. et al., "Smear Layer Removal By Means of Erbium, Chromium: Yttrium Scandium Gallium Garnet (er,Cr:YSGG) Laser Irradiatin From Apical Third of Mesial Root Canals," International Journal of Recent Scientific Research, vol. 12, Issue, 05, pp. 41804-41808, May 2021.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lukac et al.: "Photoacoustic Endodontics Using the Novel SWEEPS Er:YAG Laser Modality," Journal of the Laser and Health Academy, vol. 2017, No. 1; www.laserlaserandhealth.com.
Lukac, et al., "Modeling Photoacoustic Efficiency during Erbium Laser Endodontics," Journal of the Laser and Health Academy, vol. 2013, No. 2.
Lukac, et al., "Wavelength dependence of photoinduced photoacoustic streaming technique for root canal irrigation," Journal of Biomedical Optics 21(7), 075007 (Jul. 2016).
Lumkes, Jr., Control Strategies for Dynamic Systems: Design and Implementation, 2002, pp. 117-118.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Ma, et al.: "In vitro study of calcium hydroxide removal from mandibular molar root canals," J Endod 2015;41:553-8.
Madarati, et al.: "Efficiency of a newly designed ultrasonic unit and tips in reducing temperature rise on root surface during the removal of fractured files," J Endod 2009;35:896-9.
Madarati, et al.: "Management of intracanal separated instruments," J Endod 2013;39:569-81.
Madarati, et al.: "Qualtrough AJ. Factors contributing to the separation of endodontic files," Br Dent J 2008;204:241-5.
Matsumoto, et al. "Visualization of irrigant flow and cavitation induced by Er: YAG laser within a root canal model." Journal of endodontics 37.6 (2011): 839-843.
Maximum Dental Inc ., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Merigo, et al., "Bactericidal effect of Er,Cr:YSGG laser irradiation on endodontic biofilm: An ex vivo study," Journal of Photochemistry & Photobiology, B: Biology 218 (2021) 112185.
Molina, et al.: "Histological evaluation of root canal debridement of human molars using the GentleWaveTM system," J Endod 2015;41:1702-5.
Montero-Miralles, et al., "Comparative study of debris and smear layer removal with EDTA and Er,Cr:YSGG laser," J Clin Exp Dent. 2018;10(6):e598-602.

(56) References Cited

OTHER PUBLICATIONS

Mrochen, et al. "Erbium: yttrium-aluminum-garnet laser induced vapor bubbles as a function of the quartz fiber tip geometry Erbium: yttrium-aluminum-garnet laser induced vapor bubbles as a function of the quartz fiber tip geometry." Journal of biomedical optics 6.3 (2001): 344-350.

Nagahashi et al., "Er:YAG laser-induced cavitation can activate irrigation for the removal of intraradicular biofilm", Scientific Reports, https://doi.org/10.1038/s41598-022-08963-x, pp. 1-11 (2022).

Nammour et al.: "External temperature during KTP-nd:YAG laser irradiation in root canals: An in vitro study," Lasers in Medical Science, 19(1), 27-32, Jul. 2004.

Nevares, et al.: "Success rates for removing or bypassing fractured instruments: a prospective clinical study," J Endod 2012;38:442-4.

Ohrn et al; Geometric Effects on Spray Cone Angle for Plain-Orifice Atomizers; pp. 253-268; Atomization and Sprays, vol. 1 (1991).

Ohrn et al; Geometrical Effects on Discharge Coefficients for Plain-Orifice Atomizers; pp. 137-153; Atomization and Sprays, vol. 1, No. 2 (1991).

Olivi, et al., "Lasers in Endodontics," Scientific Background and Clinical Applications, 2016.

Oral Health, Special Issue, Laser Dentistry, Photo-Acoustic, Root Canal, Decontamination, in 52 pages.

Peeters, et al., "Measurement of temperature changes during cavitation generated by an erbium, chromium: Yttrium, scandium, gallium garnet laser," OJST. 2012;2:286-91.

Phinney, Ralph E.; The breakup of a turbulent liquid jet in a gaseous atmosphere; pp. 689-701; J. Fluid Mechanics, vol. 60, Part 4; Oct. 1973.

Piezon Master 600 Ultrasound a la carte, EMS Electro Medical Systems, EMS SA FA-319.EN ed. Mar. 2009; Brochure dated Mar. 2009, in 2 pages.

Prasad, et al., Introduction to biophotonics. John Wiley & Sons, 2003.

Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.

Ramamurthi et al; Disintegration of Liquid Jets from Sharp-Edged Nozzles; pp. 551-564; Atomization and Sprays, vol. 4 (1994).

Reitz et al; Mechanism of atomization of a liquid jet; pp. 1730-1742; Physics Fluids, vol. 25, No. 10; Oct. 1982.

Roots—international magazine of endodontics, Issn 2193-4673, vol. 15, Issue Apr. 2019.

Roth, et al.: "A study of the strength of endodonitc files: potential for torsional breakage and relative flexibility," J Endod 1983; 9:228-32.

Ruddle, "Nonsurgical retreatment," J Endod 2004;30:827-45.

Sabeti, "Healing of apical periodontitis after endodontic treatment with and without obturation in dogs," Journal of Endodontics, Jul. 2006, pp. 628-633.

Sallam et al; Liquid breakup at the surface of turbulent round liquid jets in still gases; pp. 427-449; International Journal of Multiphase Flow, vol. 28; Mar. 2002.

Sawant et al; Effect of hydrodynamic cavitation on zooplankton: A tool for disinfection; pp. 320-328; Biochemical Engineering Journal, vol. 42, Issue 3; Dec. 2008.

Schoop et al., "The impact of an erbium, chromium: yttrium-scandium-gallium-garnet laser with radial-firing tips on endodontic treatment," Lasers in Medical Science, vol. 24(1):59-65, published online Nov. 20, 2007.

Schneider, et al.: "A comparison of canal preparations in straight and curved root canals," Oral Surg Oral Med Oral Pathol 1971;32:271-5.

Schneider, et al.: "NIH Image to ImageJ: 25 years of image analysis," Nat Methods 2012;9:671-5.

Seet, et al., An in-vitro Evaluation of the Effectiveness of Endodontic Irrigants, with and without Sonic and Laser Activation, in the Eradication of Enterococcus faecalis Biofilm.

Shaheed, et al., "Healing of Apical Periodontitis after Minimally Invasive Endodontics therapy using Er, Dr:YSGG laser: A Prospective Clinical Study," Sys Rev Pharm 2020; 11(2): 135-140.

Shen, et al.: "Factors associated with the removal of fractured NiTi instruments from root canal systems," Oral Surg Oral Med Oral Pathol Oral Radiol Endod 2004;98:605-10.

Shi et al; Comparison—speed liquid jets; Experiments in Fluids, vol. 35; pp. 486-492; Oct. 7, 2003.

Silva, et al., "Analysis of Permeability and Morphology of Root Canal Dentin After ER,Cr:YSGG Laser Irradiation," Photomedicine and Laser Surgery vol. 28, No. 1, pp. 103-108, 2010.

Skyttner, "Endodontic instrument separations: evaluation of a patient cases series with separated endodontic instruments and factors related to the treatment regarding separated instruments [thesis]," Stockholm: Karolinska Institutet; 2007.

Sou et al; Effects of cavitation in a nozzle on liquid jet atomization; pp. 3575-3582; International Journal of Heat and Mass Transfer, vol. 50; Mar. 2007.

Souter, et al.: "Complications associated with fractured file removal using an ultrasonic technique," J Endod 2005;31:450-2.

Soyama et al; High-Speed Observation of Ultrahigh-Speed Submerged Water Jets; pp. 411-416; Experimental Thermal and Fluid Science, vol. 12 1996).

Soyama, Hitoshi; High-Speed Observation of a Cavitating Jet in Air; Journal of Fluids Engineering, vol. 127; pp. 1095-1101; Nov. 2005.

Stamos et al., "Retreatodontics and ultrasonics", Journal of Endodontics, vol. 14., No. 1, pp. 39-42, Jan. 1, 1988.

Stamos et al., "Use of ultrasonics in single-visit endodontic therapy," Journal of Endodontics, vol. 13, No. 5, pp. 246-249, May 1, 1987.

Summers, David A; Considerations in the Comparison of Cavitating and Plain Water Jets; pp. 178-184; Rock Mechanics and Explosive Research Center, Rolla, Missouri, 1983.

Summers, David A; The Volume Factor in Cavitation Erosion; Proceedings of 6th International Conference on Erosion by Liquid and Solid Impact; University of Missouri-Rolla; Rolla, Missouri, 1983, in 12 pages.

Suslick, K. S., et al., "The Sonochemical Hot Spot", Journal of the American Chemical Society, vol. 108, No. 18, Sep. 3, 1986, pp. 5641-5642.

Suslick, K. S., et al., "Heterogeneous Sonocatalysis with Nickel Powder", Journal of the American Chemical Society, vol. 109, No. 11, May 27, 1987, pp. 3459-3461.

Suter, et al.: "Probability of removing fractured instruments from root canals," Int Endod J 2005;38:112-23.

Tafreshi et al; Simulating Cavitation and Hydraulic Flip Inside Hydroentangling Nozzles; pp. 359-364; Textile Research Journal, vol. 74, Apr. 2004.

Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.

Tafreshi et al; The effects of nozzle geometry on waterjet breakup at high Reynolds numbers; pp. 364-371; Experiments in Fluids, vol. 35; Sep. 2, 2003.

Takeda et al., "A comparative study of the removal smear layer by three endodontic irrigants and two types of laser," International Endodontic Journal, 32, 32 39, 1999.

Takeda et al., "Comparative Study about the Removal of Smear Layer by Three Types of Laser Devices," Journal of Clinical Laser Medicine & Surgery, vol. 16, No. 2, 1998 Mary Ann Liebert, Inc, pp. 117-122.

Terauchi, et al.: "Evaluation of the efficiency of a new file removal system in comparison with two conventional systems," J. Endod 2007;33:585-8.

Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.

Ward Jr.: "The use of an ultrasonic technique to remove a fractured rotary nickel-titanium instrument from the apical third of a curved root canal," Aust Endod J 2003;29:25-30.

Wohlemuth et al.: "Effectiveness of GentleWave System in Removing Separated Instruments," JOE, vol. 41, No. 11, Nov. 2015.

(56) References Cited

OTHER PUBLICATIONS

Yoldas, et al.: "Perforation risks associated with the use of Masserann endodontic kit drills in mandibular molars," Oral Surg Oral Med Oral Pathol Oral Radiol Endod 2004;97:513-7.
Yu et al.: "Study on removal effects of filling materials and broken files from root canals using pulsed Nd:YAG laser," J Clin Laser Med Surg 2000;18:23-8.
Zehnder, "Root Canal Irrigants", Journal of Endodontics, vol. 32, No. 5, pp. 389-398, May 2006.
Zuo et al; An Attribution of Cavitation Resonance: Volumetric Oscillations of Cloud; pp. 152-158; Journal of Hydrodynamics, vol. 21; Apr. 2009.
European Extended Search Report, re EP Application No. 14765398.4, dated May 31, 2017.
European Supplemental Search Report, re EP Application No. 07837261.2, dated May 3, 2012.
International Search Report and Written Opinion, re PCT Application No. PCT/US07/18664, dated Sep. 23, 2008.
International Preliminary Report on Patentability, re PCT Application No. PCT/US07/18664, dated Feb. 24, 2009.
International Search Report and Written Opinion, re PCT Application No. PCT/US2014/030435, dated Aug. 28, 2014.
International Preliminary Report on Patentability, re PCT Application No. PCT/US2014/030435, dated Sep. 15, 2015.
International Preliminary Report on Patentability, re PCT Application No. PCT/IL2013/050330, dated Oct. 30, 2014.
International Preliminary Report on Patentability, re PCT Application No. PCT/IL2014/050924, dated May 6, 2016.
International Search Report and Written Opinion, re PCT Application No. PCT/IL2013/050330, dated Jul. 30, 2013.
International Search Report and Written Opinion, re PCT Application No. PCT/IL2014/050924, dated Mar. 19, 2015.
International Search Report and Written Opinion for PCT/US2021/053844, dated Mar. 11, 2022, in 22 pages.
Abad-Gallegos et al, "In vitro evaluation of the temperature increment at the external root surface after Er,Cr:YSGG laser irradiation of the root canal", Med Oral Patol Oral Cir Bucal, vol. 14(12):658-662 (2009).
Abdelkarim-Elafifi et al., "Aerosols generation using Er,Cr:YSGG laser compared to rotary instruments in conservative dentistry: A preliminary study", J Clin Exp Dent, vol. 13(1):e30-6 (2021).
Altundasar et al., "Ultramorphological and histochemical changes after ER,CR:YSGG laser irradiation and two different irrigation regimes", Basic Research—Technology, vol. 32(5):465-468 (2006).
Arnabat et al., "Bactericidal activity of erbium, chromium: yttrium-scandium-gallium-garnet laser in root canals", Lasers Med Sci vol. 25:805-810 (2010).
Aydin et al., "Efficacy of erbium, chromium-doped yttrium, scandium, gallium and garnet laser-activated irrigation compared with passive ultrasonic irrigation, conventional irrigation, and photodynamic therapy against *enterococcus faecalis*", ResearchGate, https://www.researchgate.net/publication/338906248, Article in The Journal of Contemporary Dental Practice, Jan. 2020.
Beader et al., "Efficacy of three different lasers on eradication of enterococcus faecalis and candida albicans biofilms in root canal system", ResearchGate, https://www.researchgate.net/publication/316287465, Article in Photomedicine and Laser Surgery, Apr. 2017.
Betancourt et al., "Er,Cr:YSGG laser-activated irrigation and passive ultrasonic irrigation: comparison of two strategies for root canal disinfection", Photobiomodulation, Photomedicine, and Laser Surgery, vol. 383(2):91-97 (2020).
Betancourt et al., "ER/Cr:YSGG laser-activation enhances antimicrobial and antibiofilm action of low concentrations of sodium hypochlorite in root canals", Antibiotics, vol. 8(232):1-10 (2019).
Bolhari et al., "Efficacy of Er,Cr:YSGG laser in removing smear layer and debris with two different output powers", Photomedicine and Laser Surgery, vol. 32(10):527-532 (2014).
Cheng et al., "Evaluation of the bactericidal effect of Nd:YAG, Er:YAG, Er,Cr:YSGG laser radiation, and antimicrobial photodynamic therapy (aPDT) in experimentally infected root canals", Lasers in Surgery and Medicine, vol. 44:824-831 (2012).
Christo et al., "Efficacy of low concentrations of sodium hypochlorite and low-powered Er,Cr:YSGG laser activated irrigation against an *Enterococcus faecalis* biofilm", International Endodontic Journal, vol. 49:279-286 (2016).
De Moor et al., "Laser induced explosive vapor and cavitation resulting in effective irrigation of the root canal. Part 2: Evaluation of the efficacy", Lasers in Surgery and Medicine, vol. 41:520-523 (2009).
De Moor et al., "Efficacy of ultrasonic versus laser-activated irrigation to remove artificially placed dentin debris plugs", Basic Research Technology, JOE vol. 36(9):1580-1583 (2010).
Dewsnup et al., "Comparison of bacterial reduction in straight and curved canals using erbium, chromium:Yttrium-Scandium-Gallium-Garnet laser treatment versus a traditional irrigation technique with sodium hypochlorite", Basich Research—Technology, JOE, vol. 36(4):725-728 (2010).
Erken, "Evaluation of apically extruded debris using two niti systems associated with two irrigation techniques in primary teeth", ResearchGate, https://www.researchgate.net/publication/310465261, The Journal of Clinical Pediatric Dentistry, Nov. 2016.
George et al., "Laser activation of endodontic irrigants with improved conical laser fiber tips for removing smear layer in the apical third of the root canal", Basic Research—Technology, JOE, vol. 34(12):1524-1521 (2008).
George et al., Apical extrusion of root canal irrigants when using Er:YAG and ER,Cr:YSGG lasers with optical fibers: An in vitro dye study, Basic Research—Technology, JOE, vol. 34(6):706-708 (2008).
Ishizaki et al., "Thermographical and morphological studies of Er,Cr:YSFF laser irradiation on root canal walls", Photomedicine and Laser Surgery, vol. 22(4):291-297 (2004).
Kustarci et al., "Efficacy of laser activated irrigation on apically extruded debris with different preparation systems", Photomedicine and Laser Surgery, vol. 33(7):384-389 (2015).
Licata et al., "Effectiveness of a new method of disinfecting the root canal, using Er,Cr:YSGG laser to kill Enterococcus faecaslis in an infected tooth model", ResearchGate, https://www.researchgate.net/publication/255688995, Article in Lasers in Medical Science, Aug. 2013.
Lopes et al., "Evaluation of chemical and morphological changes in radicular dentin after different final surface treatments", Micros. Res. Tech. vol. 81:973-979 (2018).
Martins et al., "Outcome of Er,Cr:YSGG laser-assisted treatment of teeth with apical periodontitis: A blind randomized clinical trial", Photomedicine and Laser Surgery, vol. 32(1):3-9, (2014).
Martins et al., "Efficacy of Er,Cr:YSGG laser with endodontical radial firing tips on the outcome of endodontic treatment: blind randomized controlled clinical trial with six-month evaluation", Lasers Med Sci vol. 28:1049-1055 (2013).
Matsuoka et al., "Morphological study of the Er,Cr:YSGG laser for root canal preparation in mandibular incisors with curved root canals", Photomedicine and Laser Surgery, vol. 23(5):480-484 (2005).
Minas et al, "In vitro investigation of intra-canal dentine-laser beam interaction aspects: II. Evaluation of ablation zone extent and morphology", Lasers Med Sci vol. 25:867-872 (2010).
Nasher et al., "Debris and smear layer removal in curved root canals using the dual wavelength Er,Cr:YSGG/Diode 940 nm laser and the XP_Endoshaper and finisher technique", ResearchGate, https://www.researchgate.net/publication/338755431, Article in Photobiomodulation Photomedicine and Laser Surgery, Jan. 2020.
Nowazesh et al., "Efficacy of root canal preparation by Er,Cr:YSGG laser irradiation with crown-down technique in Vitro", Photomedicine and Laser Surgery, vol. 23(2):196-201 (2005).
Peeters et al., "Efficacy of smear layer removal at the root tip by using ethylenediaminetetraacetic acid and erbium, chromium: Yttrium, candium, and gallium garnet laser", Basic Research—Technology, JOE, vol. 37(11):1585-1589 (2011).
Peeters et al., "Extrusion of irrigant in open apex teeth with periapical lesions following laser-activated irrigation and passive ultrasonic irrigation", Iranian Endodontic Journal, vol. 13(2):169-175 (2018).

(56) References Cited

OTHER PUBLICATIONS

Peeters et al., "Measurement of pressure changes during laser-activated irrigant by an erbium, chronium: yttrium, scandium, gallium, garnet laser", Lasers in Medical Science, DOI 10.1007/s10103-014-1605-5, Received Jan. 23, 2014, Springer-Verlag London.
Peeters et al., "Radiographic examination of apical extrusion of root canal irrigants during cavitation induced by Er,Cr:YSGG laser irradiation: an in vivo study", Clin Oral Invest vol. 17:2105-2112 (2013).
Race et al., "Efficacy of laser and ultrasonic-activated irrigation on eradicating a mixed-species biofilm in human mesial roots", Australian Endodontic Journal, vol. 45:317-324 (2019).
Rahimi et al., "Comparison of the effect of Er,Cr-YSGG laser ultrasonic retrograde root-end cavity preparation on the integrity of root apices", Journal of Oral Science, vol. 52(1):77-81 (2010).
Schoop et al., "The use of the erbium, chromium:yttrium-scandium-gallium-garnet laser in endodontic treatment", JADA, vol. 138:949-955 (2007).
Sen et al., "Comparative safety of needle, EndoActivator, and laser-activated irrigation in overinstrumented root canals", Photomedicine and Laser Surgery, vol. 36(4):198-202 (2018).
Sigma-Aldrich, Product Specification, 2-propanol SDS, Product No. 190764.
Soares et al., "Impact of Er,Cr:YSGG laser therapy on the cleanliness of the root canal walls of primary teeth", Basic Research—Technology, JOE, vol. 34(4):474-477 (2008).
Tokuc et al., "The bactericidal effect of 2780 nm Er,Cr:YSGG laser combined with 940 nm diode laser in *enterococcus faecalis* elimination: A comparative study", Photobiomodulation, hotomedicine, and Laser Surgery, vol. XX(XX):1-6 (2019).
Wang et al., "Evaluation of the bactericidal effect of Er,Cr:YSGG, and Nd:YAG lasers in experimentallyl infected root canals", Basic Research—Biology, JOE, vol. 33(7):830-832 (2007).
Yamazaki et al., "Effects of erbium,chromium:YSGG laser irradiation on root canal walls: A scanning electron microscopic and thermographic study", Journal of Endodontics, vol. 27(1):9-12 (2001).
European Search Report, re EP Application No. 13763534.8, dated Jun. 20, 2022.
International Search Report and Written Opinion for PCT/US2021/072194, dated Jan. 27, 2022, in 15 pages.
European Extended Search Report, EP Application No. 20176387.7, dated Nov. 10, 2020.
Extended European Search Report and Written Opinion for European Application No. 21175783.6, dated Dec. 13, 2013, in 8 pages.
Extended European Search Report for European Application No. 22167511.9, dated Aug. 11, 2022, in 8 pages.
European Search Report in application No. EP 21160099.4, dated Sep. 26, 2022.
Acharya Letter Re: *PIPStek, LLC* v. *Biolase, Inc.* (D. Del. Case No. 1:23-cv-00011-MN), dated Mar. 3, 2023 in 3 pages.
Acharya Letter, Exhibit A, in 34 pages, dated Mar. 3, 2023.
Acharya Letter, Exhibit B, in 15 pages, dated Mar. 3, 2023.
Acharya Letter, Exhibit C, Waterlase User Manual, in 50 pages. For purposes of examination, consider dated 2003.
Acharya Letter, Exhibit D, Waterlase User Manual, in 79 pages. For purposes of examination, consider dated 2004.
Acharya Letter, Exhibit E, Endolase Instructions for Use, in 2 pages. For purposes of examination, consider dated 2002.
Acharya Letter, Exhibit F, Fax Boutoussov to De Vito [sic], in 2 pages. For purposes of examination, consider dated May 26, 2004.
Acharya Letter, Exhibit G, Fax Boutoussov to DiVito, in 1 page. For purposes of examination, consider dated Jun. 8, 2004.
Acharya Letter, Exhibit H, Biolase Accessories Overview, in 39 pages. For purposes of examination, consider dated Jan. 2004.
Acharya Letter, Exhibit I, Rocky Mountain Symposium, in 1 page. For purposes of examination, consider dated 2004.
Correspondence DiVito to Boutoussov, in 3 pages. For purposes of examination, consider dated May 28, 2004.
Fax Boutoussov to De Vito [sic], in 1 page. For purposes of examination, consider dated Nov. 24, 2004.

\* cited by examiner

DENTAL AND MEDICAL TREATMENTS AND PROCEDURES

This application is a continuation of application Ser. No. 17/317,744, filed May 11, 2021 (now U.S. Pat. No. 11,426, 239), which is a continuation of application Ser. No. 14/537, 742, filed Nov. 10, 2014, which is a continuation in part of application Ser. No. 14/077,880, filed Nov. 12, 2013, which is a continuation of application Ser. No. 13/633,096, filed Oct. 1, 2012, which is a continuation of application Ser. No. 12/875,565, filed Sep. 3, 2010, which is a continuation in part of application Ser. No. 11/895,404, filed Aug. 24, 2007, the entire contents of each of which are incorporated by reference herein. Application Ser. No. 12/875,565 is also a continuation in part of application Ser. No. 12/395,643, filed Feb. 28, 2009, which is a continuation in part of application Ser. No. 11/895,404, filed Aug. 24, 2007, the entire contents of each of which are incorporated by reference herein. Application Ser. No. 12/395,643 is also a continuation in part of application Ser. No. 11/704,655, filed Feb. 9, 2007, which claims priority to Provisional Application No. 60/840, 282, filed Aug. 24, 2006, the entire contents of each of which are incorporated by reference herein. Application Ser. No. 11/895,404 is a continuation in part of application Ser. No. 11/704,655 and also claims priority to Provisional Application No. 60/840,282, the entire contents of each of which are incorporated herein by reference.

FIELD OF THE INVENTION

The present invention is related to the field of dentistry, medicine and veterinary medicine.

BACKGROUND OF THE INVENTION

In the field of dentistry, one of the most important and delicate procedures is that of cleaning or extirpating a diseased root canal to provide a cavity which is substantially free of diseased tissue and antiseptically prepared for a permanent embalming or obturation to seal off the area. When done properly, this step enables subsequent substantially complete filling of the canal with biologically inert or restorative material (i.e., obturation) 1, without entrapping noxious tissue in the canal that could lead to failure of the therapy.

In a typical root canal procedure, the sequence is extirpation of diseased tissue and debris from and adjacent the canal followed by obturation. Often there is an intermediate filling of the canal with a calcium hydroxide paste for sterilization and reduction of inflammation prior to obturation and final crowning. In performing the extirpation procedure, the dentist must gain access to the entire canal, shaping it as appropriate. However, root canals often are very small in diameter, and they are sometimes quite curved with irregular dimensions and configurations. It is therefore often very difficult to gain access to the full length of the canal and to properly work all surfaces of the canal wall.

Many tools have been designed to perform the difficult task of cleaning and shaping root canals. Historically, dentists have used elongate, tapered endodontic files with helical cutting edges to remove the soft and hard material from within and adjacent the root canal area, Such root canal dental procedures often result in overly aggressive drilling and filing away of otherwise healthy dentin wall or physical structure of the tooth root thereby unduly weakening the integrity or strength of the tooth. Additionally, when performing root canal procedures, it is desirable to efficiently debride or render harmless all dead, damaged, or infected tissue and to kW all bacteria, viruses and/or other undesirable biological material within the root canal system, Illustrations of a typical root canal system are shown in FIGS. 1A and 1B. The mot canal system includes the main root canal 1 and many lateral or accessory canals 3 that branch off of the main canal 1, all of which can contain diseased or dead tissue, bacteria, etc., It is common during root canal procedure to mechanically strip out the main canal nerve, often tearing it away from the lateral canal nerves, much of which can then stay in place in the canal and become the source of later trouble, Thereafter, the main canal 1 is cleaned and extirpated with a tapered file. While it is desirable to extirpate all of the main and accessory canals in a root canal system, some of the lateral canals 3 are very small and extremely difficult to reach in order to remove tissue. Such lateral canals are often perpendicular to the main canal and may bend, twist, and change cross-section as they branch off from the main canal, making them practically inaccessible to extirpation with any known file or other mechanical device. Accordingly, lateral canals are often not properly extirpated or cleaned. Many times no effort is made in this regard, relying instead on chemical destruction and embalming processes to seal off material remaining in these areas, This approach is sometimes a source of catastrophic failure that can lead to loss of the tooth and other problems. Further, when the main canal is extirpated with a tapered file, this action can leave an undesirable smear layer along the main canal which can plug some of the lateral canal openings and cause other problems that trap noxious material against later efforts to chemically disinfect the canal.

Dentists can attempt to chemo-mechanically debride and/or sterilize both main and lateral canals using a sodium hypochlorite solution or various other medicaments that are left in the root canal system for 30 to 45 minutes a time following primary mechanical extirpation of nerve and pulp tissue. However, this approach does not necessarily completely debride or render harmless ail of the lateral root canals and material trapped therein because of the difficulty in cleaning off the smear layer and/or negotiating and fully wetting the solution into some of the smaller twisted lateral canals. As a result, many treatments using this method fail over time due to reoccurring pathology. This often requires retreatment and sometimes loss of the tooth.

Attempts have been made to reduce or eliminate the use of endodontic files and associated drawbacks by using lasers in the performance of root canal therapy. Some of these approaches involve burning away or carbonizing diseased and other tissue, bacteria, and the like within the canal. In these approaches, laser light is said to be directed or focused into or onto the diseased tissue, producing very high temperatures that intensely burn, carbonize, ablate, and destroy the tissue. These ablative treatments using high thermal energy to remove tissue often result in damage to the underlying collagen fibers and dentin of the root 5, even fusing the hydroxyapatite which makes up the dentin. In some cases, such treatments can cause substantial heating of the periodontal material and bone 7 surrounding the tooth, potentially causing necrosis of the bone and surrounding tissue. Additionally, the high temperatures in such treatments can melt the walls of the main canal, often sealing off lateral canals, thereby preventing subsequent treatment of lateral canals, Other attempts to use lasers fix root canal therapy have focused laser light to a focal point within fluid disposed within a root canal to boil the fluid. The vaporizing fluid creates bubbles which erode material from the root canal when they implode. Such treatments which must raise the fluid temperature above the latent heat of vaporization significantly elevate the temperature of the fluid which can also melt portions of the main canal and cause thermal damage to the underlying dentin, collagen, and periodontal tissue. The damage caused to the tooth structure by these high energy ablative laser treatments weakens the integrity or strength of the tooth, similar to endodontic treatment utilizing endodontic files.

Therefore, there is a present and continuing need for minimally invasive, biomemetic, dental and medical therapies which remove diseased tissue and bacteria from the main root canal as well as the lateral canals of the root canal system while leaving the biological structures undamaged and substantially intact.

SUMMARY OF INVENTION

It is an object of the present invention to provide new medical, dental and veterinary devices, treatments and procedures.

It is another object of the present invention to provide a device for producing a photoacoustic wave used in endodontal treatment of tooth interiors comprising a laser system having a wavelength of at least 1500 nm and power of at least 0.5 Watt, a sheath coupled at one end to the laser system said sheath comprising a laser fiber optic and a treatment fluid lumen, both running the length of the sheath and exiting the sheath at a distal end, said laser fiber optic having a flat, blunt or modified tip and whereby inserting the tip into the treatment fluid delivered into root canal produces a photoacoustic wave as the laser is pulsed.

It is yet another object of the present invention to provide a method for endodontal treatment of tooth interiors comprising the steps of: providing a laser having a wavelength of at least 1500 nm and at least 0.5 Watt; providing a laser fiber optic coupled to the laser, said laser fiber optic having a flat, blunt or modified tip; inserting the tip of the laser fiber optic into a root canal in a tooth; treating the interior root canal by creating a photoacoustic wave front in the interior of the root canal using the at least 1500 nm at least 0.5 Watt laser energy; withdrawing the tip of the laser fiber optic from the root canal; and sealing root canal.

In accordance with one embodiment of the present invention, a method is provided for treating a root canal in a tooth containing a crown portion extending to above a gum line and one or more elongate roots integral with and projecting from the crown into the gum and an adjacent jaw bone. Each root has a root canal containing pulp including nerve and other tissue in open communication with a pulp or coronal chamber in the crown. An opening is formed in the crown into the pulp chamber dimensioned to enable working access to a canal of said one or more roots for treatment thereof. Pulp is removed from the pulp chamber to provide an open area therein to gain access to pulp in said canal and, optionally, remove at least pan of the pulp from said canal to make an opening in said canal in flow communication with said open area in said pulp chamber. Liquid containing hydroxyl groups is dispensed into at least the open area in the pulp chamber in an amount sufficient to provide a liquid reservoir.

A laser system is provided containing a source of a laser light beam and an elongate optical fiber connected to said source and configured to transmit said laser light beam to a tip portion thereof: The tip may include a tapered tip tapering to an apex with a surrounding conical wall, substantially the entire surface of which is uncovered so that said laser light beam is emitted therefrom generally omnidirectionally, The optical fiber may also contain cladding in the form of a continuous sheath coating extending from the source to a terminus edge spaced proximally from said apex of said tapered tip toward said source by a distance of from about 2 to about 10 millimeters so that the surface of said optical fiber is uncovered over the entirety of said tapered tip and over any part of a cylindrical outer surface of the fiber between the terminus and the beginning of the tapered end.

The tip of the laser is substantially completely immerse into the liquid reservoir, and pulsing said laser source at a power level of from about 0.1 W to about 1.5 W and at a pulse duration of from about 50 to about 1000 microseconds, at a pulse frequency of from about 2 Hz to about 25 Hz, and for a cycle time of from about 10 to about 40 seconds.

DETAILED DESCRIPTION OF THE DRAWINGS

FIGS. 1a and 1b illustrate a root canal system including a main or primary root canal and lateral and sub-lateral canals that branch off of the main canal. Some of these lateral canals are very small and extremely difficult to reach in order to eliminate any bacteria and/or viruses. Such lateral canals may bend, twist, change cross-section and/or become long and small as they branch off from the main canal, making them very difficult to access or target therapeutically.

FIG. 2 is a Scanning Electron Micrograph (SEM) clearly illustrating internal reticular canal wall surfaces following use of the present invention which, as can be seen, are preserved with no burning, melting, or other alteration of the canal wall structure or loss of its porosity after subtraction of the internal tissue. The surfaces retain high porosity and surface area and are disinfected for subsequent filling and embalming, i.e., using rubber, gutta-percha, latex, resin, etc.

DESCRIPTION OF THE PREFERRED EMBODIMENTS

Figure 1A:
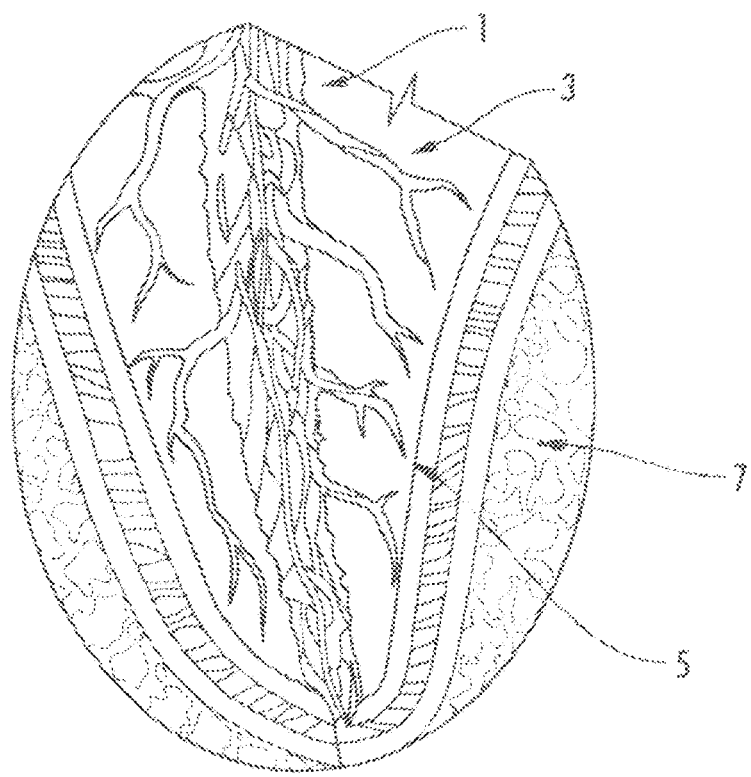
Figure 1B:
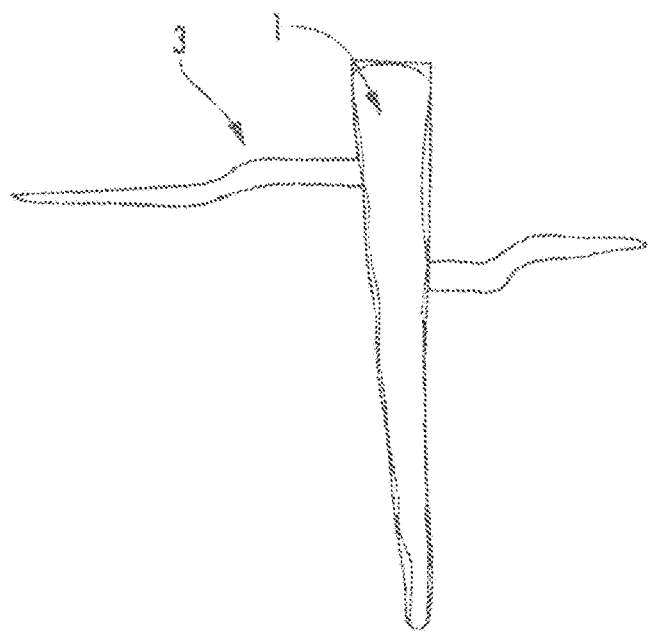
Figure 2:
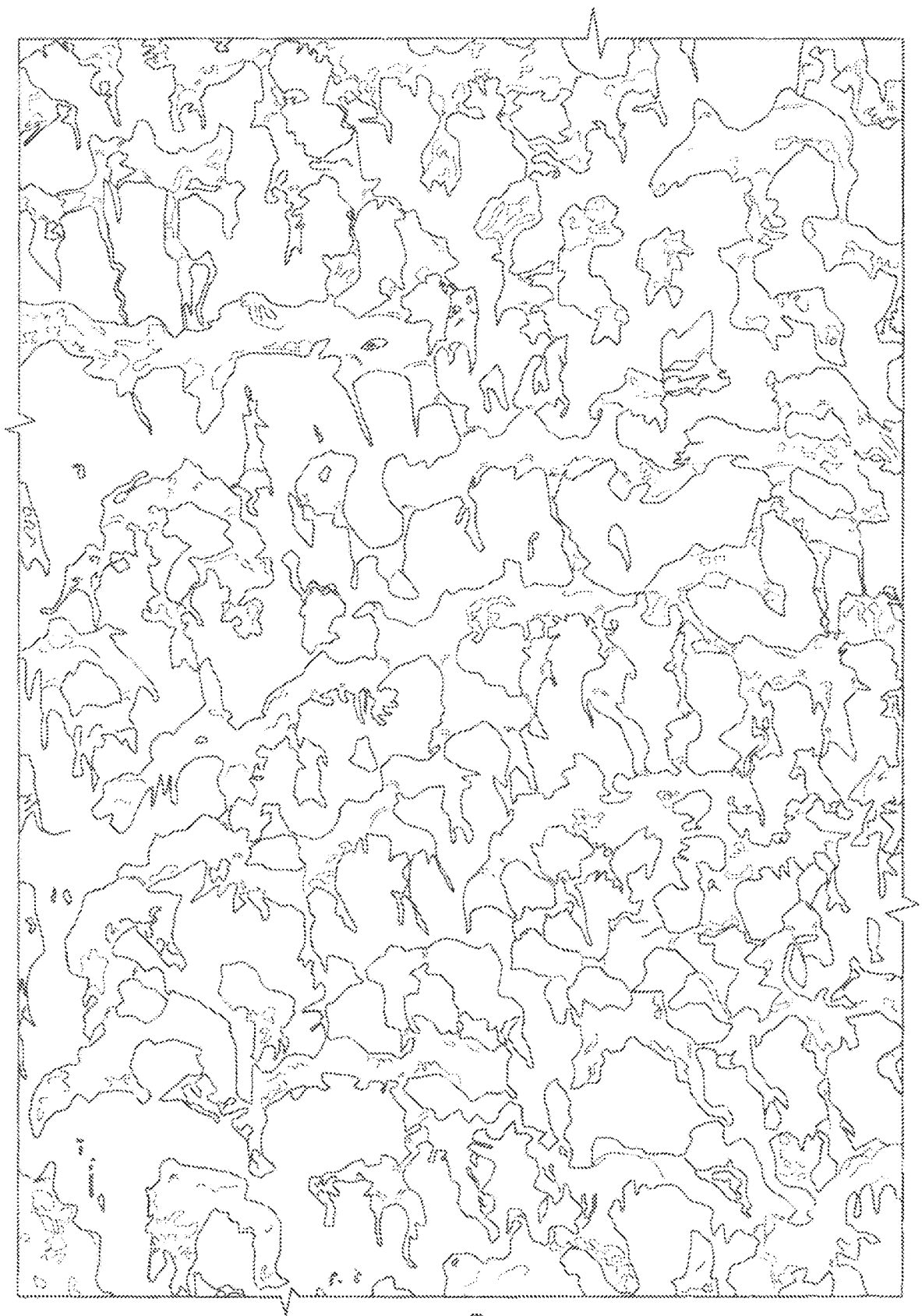

The present invention is useful for treating dental, medical, and veterinary problems; primarily dental surface and nerve preparations. The present invention uses nanotechnology and/or microtechnology in dental, medical, and veterinary application during procedures that otherwise face reoccurring infection, inefficient performance and at an increase in expenses. The result of this invention has the potential to decrease the patient chair time by over 50%, thereby reducing the cost of the procedure to the practitioner and reducing the potential for future failures over time.

The overall scheme according to the present invention comprises a first solution that is introduced into nerve tissue, typically in a tooth. The first solution enlarges and porositizes the nerve tissue. Most, if not all, of the nerve is mechanically removed from the tooth by the forces produced by the expanding tissue on the tapered walls. A second solution is introduced into the canal left by the optionally removed the nerve tissue, which dissolves any remaining nerve tissue and debrides the accompanying area. The porosity of the tissue allows for rapid penetration of fluids.

The first dispensed solution comprises a carrier, a source of oxygen and a sensitizing agent. The carrier is preferably water, paste, foam and or gel or a combination of the like. The source of oxygen is preferably an oxidizing bleach agent, such as sodium hypochlorite, perborate or peroxide and the like. The sensitizing agent is preferably a nano- or micro-structure as exemplified by fullerenes, such as nanotubes or buckyballs, or other nanodevices (including micro-sized) capable of sensitizing the oxygenating or activated or activatable chemical, e.g., oxidative bleaching agent.

The sensitizing is accomplished when the first solution is applied to a targeted area directly or with mechanical, physical or other assistance such as mild vibrational or ultrasonic stimulation. The sensitizer is then activated by an energy source, such as photons (light), acoustic (ultrasonic), photo-acoustic, thermo-acoustic, electromagnetic or other phenomena that transitions the sensitizer from a ground state to a higher energy state (singlet state). Typically the singlet state is converted into a triplet state via an intersystem crossing mechanism. The energy difference between the triplet state and the ground state is transferred to the ground state of the. oxygen source and as a result highly reactive singlet oxygen is formed (type II photodynamic reaction). Presumably, the singlet oxygen expands and porositizes the nerve tissue.

The first solution can preferably include additional effective ingredients such as surfactants to reduce the surface tension of the solution and act as a lubricant between the nerves and the canals; antibiotics; stabilizers; polar, non-polar solvents, and the like.

This same methodology can also be used with chemical constituents other than singlet oxygen that are released by various forms of imparted energy.

Preferred energy sources include, but are not limited to; sonic, ultrasonics, electromagnetic, optical, micromechanical stirring or other similar forms that can impart energy to the fluid or combination of these, which is absorbed by the sensitizer structure and creates a resultant reaction.

The most preferred embodiment of the energy source is a pulsed laser light that is photoacoustically coupled to the first solution. The laser light is delivered using a commercially available laser source and an optical light fiber attached at a proximate end to the laser source and has an application tip at the distal end. The application tip may be flat, but is preferably a beveled or tapered tip having a taper angle between 30 and 36 degrees. Preferably any cladding on the optic fiber is stripped from approximately 5 mm of the distal end. The taper angle of the fiber tip and removal of the cladding provide improved lateral dispersion of the emitted laser light and photoacoustic effect.

It was found that the photoacoustic coupling of the laser light to the first solution provides enhanced penetration of the first solution into the surrounding tissue and accessory canals, thereby allowing an excited oxygen source to reach areas of the canal system that are not accessible to laser light alone.

In another use for the present invention is in the field of dental carries or cavities. X-ray identifies a carrier. The carrie is entered using a minimal event (small drillbit or laser drilled holes), the first solution is added and activated, the activated solution arrests, cleans and debides the pathological malady without according damage to the healthy tissue. After the first solution cleans the tooth area interior or affected carrie, the used solution is removed from the carrie, a second X-ray may be performed with or without a radio-opaque fluid that is introduced into the carrie to identify the extent of cleaning performed by the first solution. The first solution may be reintroduced into the carrie in order to further clean the interior, as necessary. After the carrie has been determined to be clean and free from infection, it may then be filled according to current dental practices with only a small hole to seal on the surface.

An alternate method for introducing the first and/or second solutions would be to use vacuum enhanced delivery methods. One such method would be to apply a vacuum to the root canal, thereby removing any included solution, then introducing either the first or second solution into the vacuum-vacated canal, thereby using atmospheric pressure to force the solution into small and typically inaccessible areas. This vacuum/pressure methodology can also be applicable to more effectively infusing the filling materials.

This same methodology has the potential for use with other chemical species that do not require the use of the nanotubes, but whose molecules react with the inherent energy and whose molecules produce similar effects to those previously mentioned above, i.e. expansion, debridement, etc.

In addition to expansion and porositizing the nerve tissue, it is found that the first solution also mechanically abrades, cleans and debrides the surface of the canal or tissues. Resultant Scanning Electron Micrographs (SEM's) show the reticular surface of the dentin to be devoid of infection and malady and allowing for rinsed removal of the debris elements.

Figure 3A:
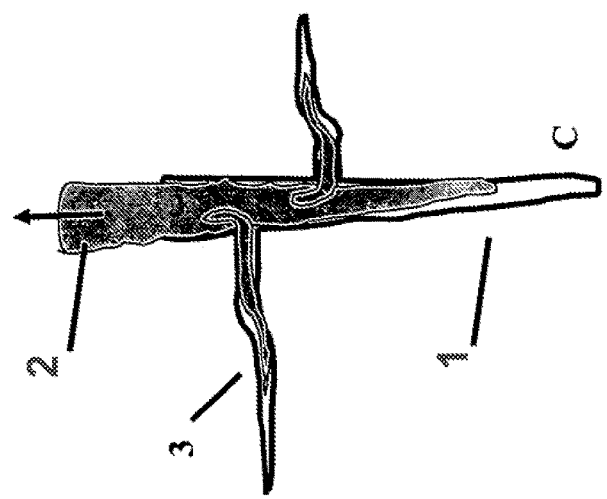
FIG. 3A illustrates a more preferred approach using the current invention, including optical activation.
Figure 3A:
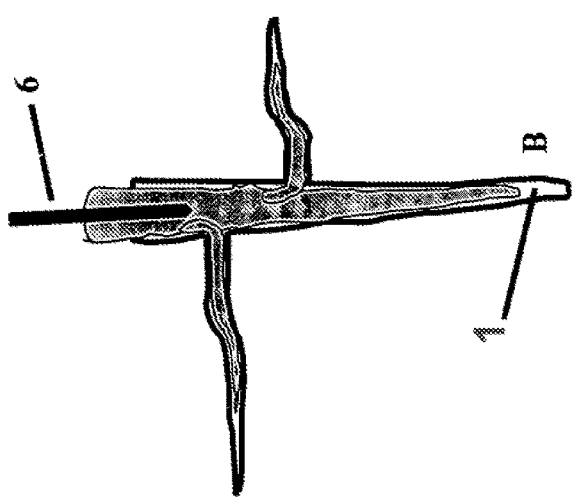
Figure 3A:
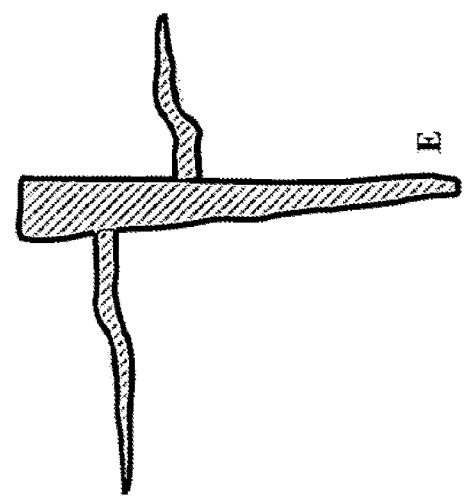
Figure 3A:
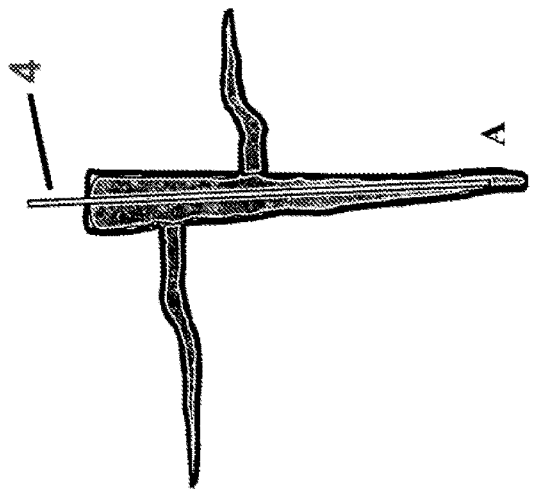
Figure 3A:
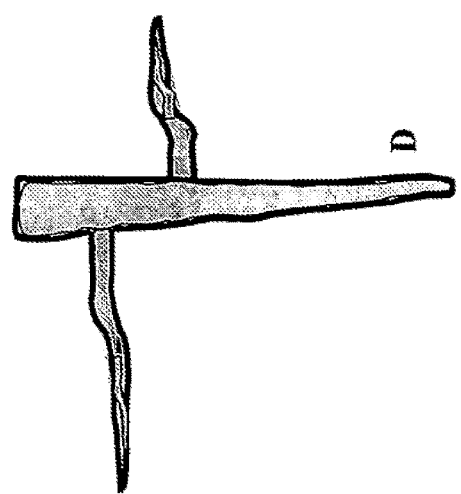

FIG. 3A illustrates a more preferred approach using the invention. A. The first solution, which containing the nanotechnology, is slowly dispensed into the main root nerve and canal, 2 and 1, respectively, using a syringe 4 with nerve 2 still intact (no filing required) and allowed to penetrate into accessory nerve canals 3. B. An activating energy source 6, in this approach photo-acoustic, is applied. C. The nanotechnology is activated by the energy source 6 thereby expanding the dental root nerve tissue 2 (up to 10-fold) and hydraulically forcing a portion of the nerve 2, along with a portion of the accessory nerve out of the tapered root structure and the accessory nerve out of the accessory canals. Simultaneously, the nerve tissue 2 becomes more porous allowing more agent access to repeat the process. D. The enlarged nerve 2 is optionally removed from the root canal 1. The second solution is added with to complete tissue decomposition. E. The cavity is then rinsed and filled and sealed (crosshatched).

Figure 3B:
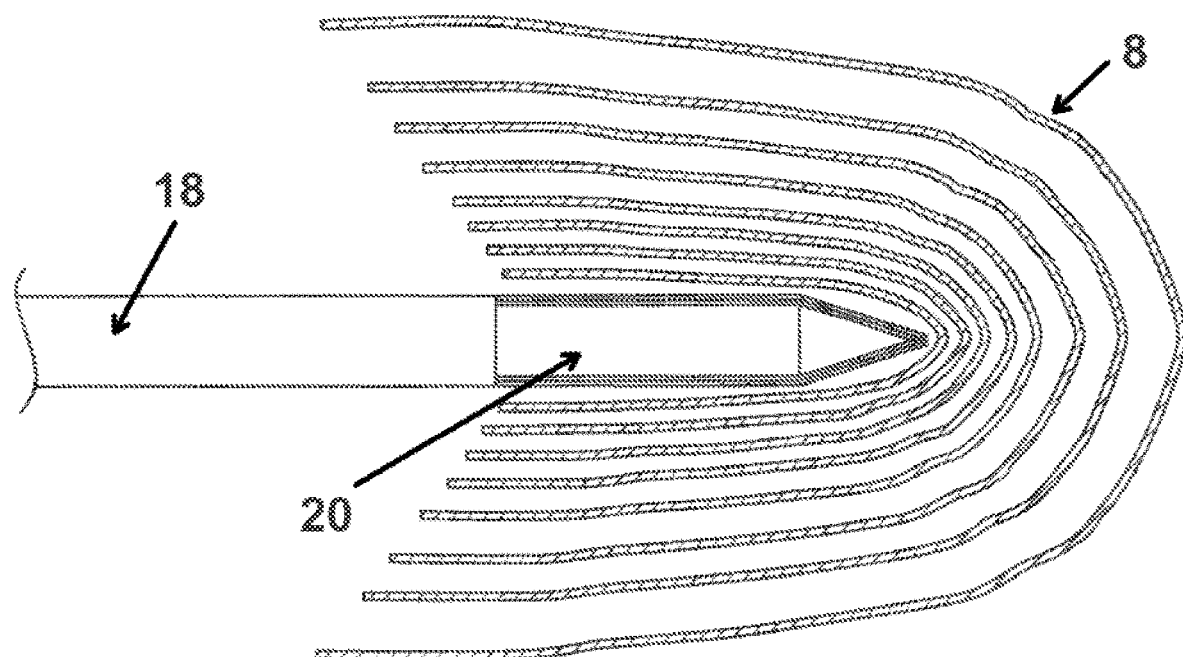
FIG. 3B is a graphical illustration of features of a laser fiber tip configured according to a preferred embodiment of the present invention.
Figure 4:
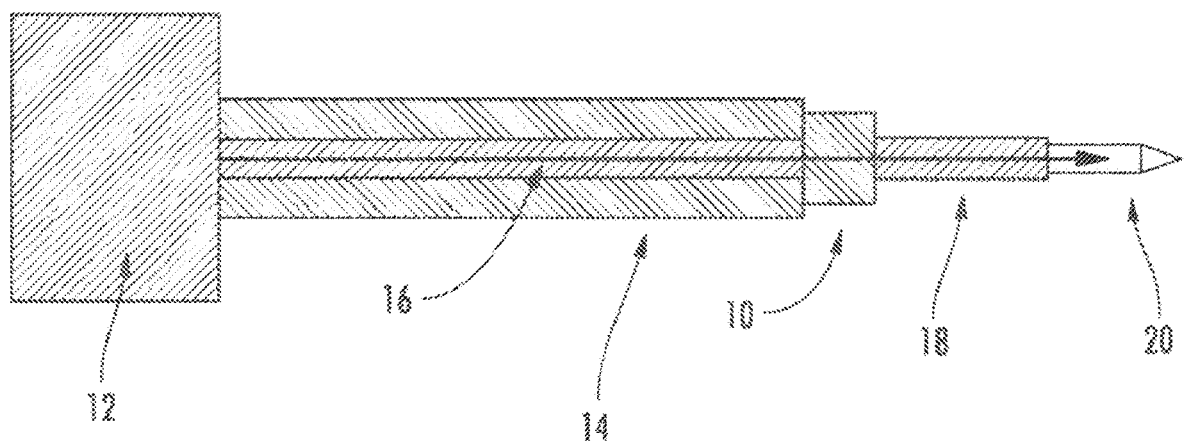
FIG. 4 is a graphical illustration of a laser system according to an embodiment of the present invention.
Figure 5:
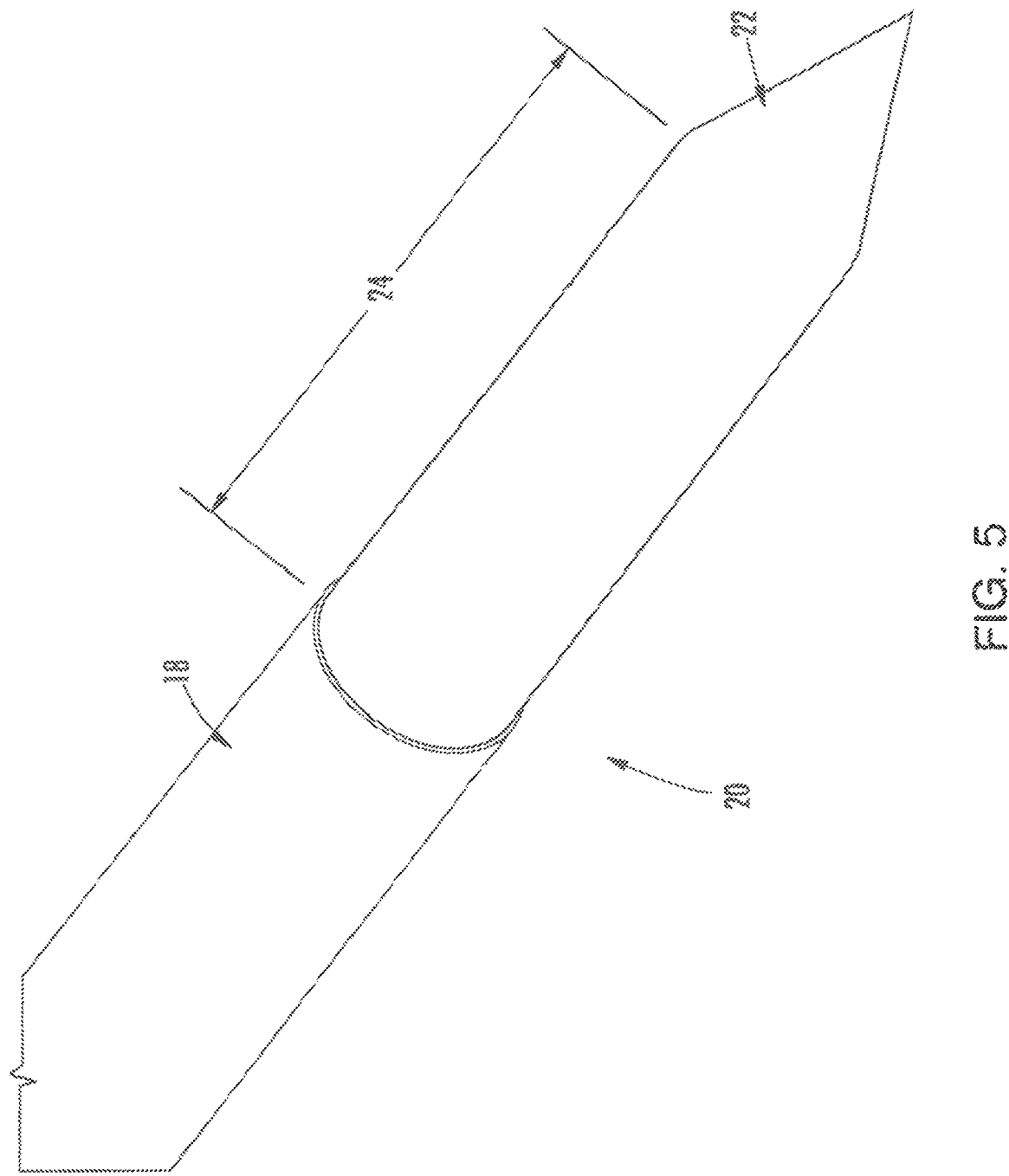
FIG. 5 is a graphical illustration of an applicator tip of a laser system according to an embodiment of the invention.
Figure 6:
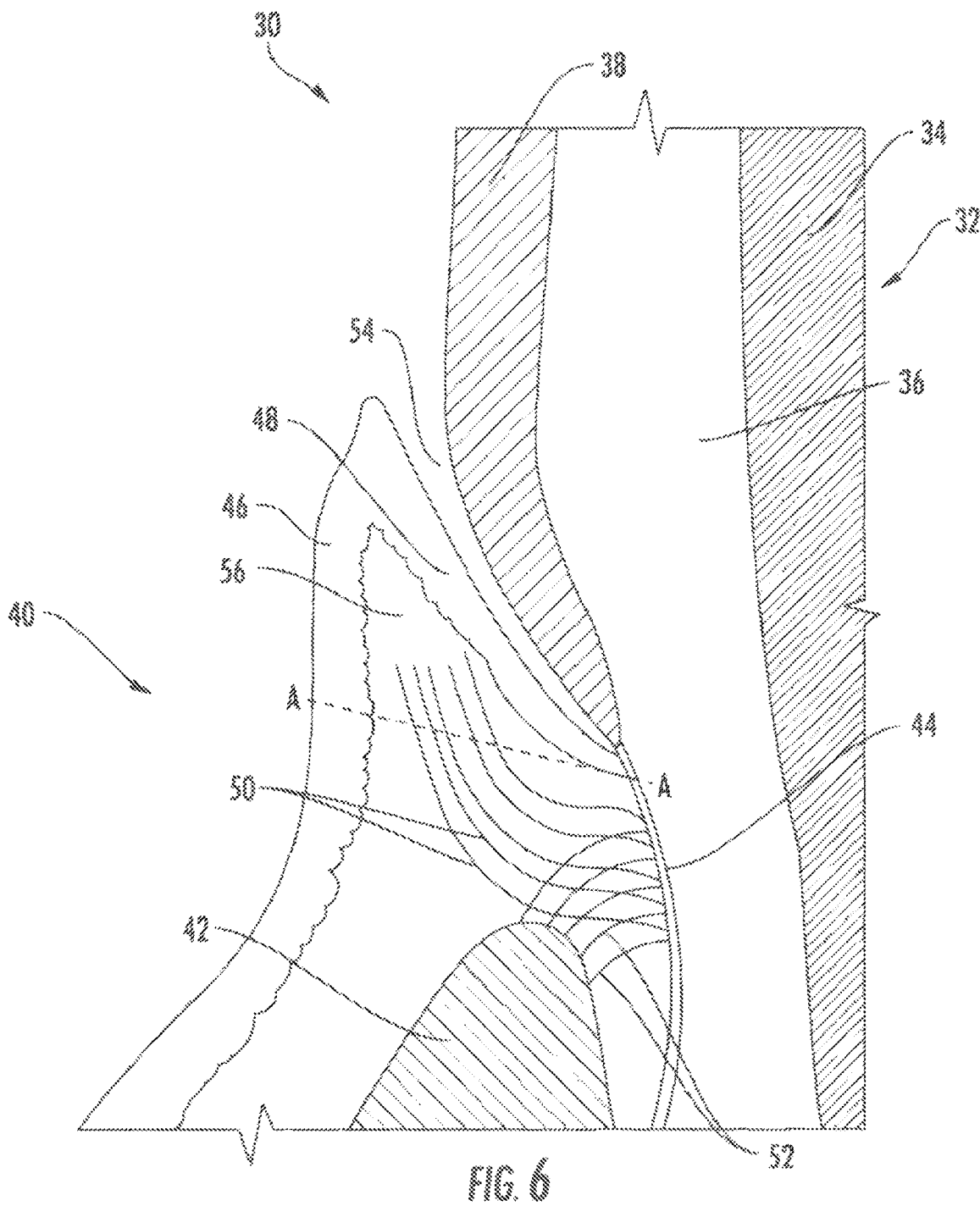
FIG. 6 shows a somewhat schematic cutaway view of a tooth and healthy surrounding gum tissue.
Figure 7:
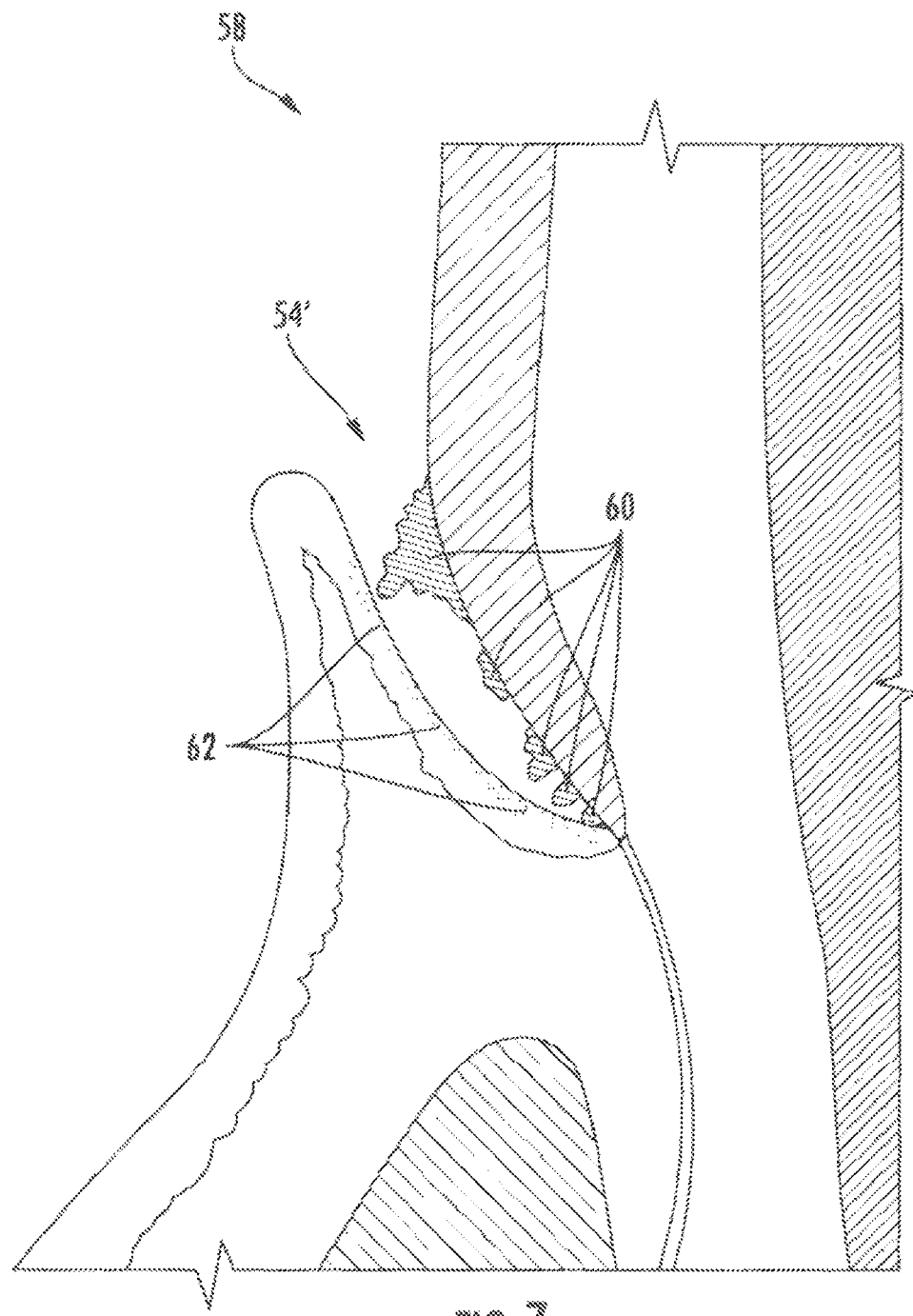
FIG. 7 shows a somewhat schematic cutaway view of a tooth and surrounding gum tissue including calculus deposits and partially diseased epithelium.
Figure 8:
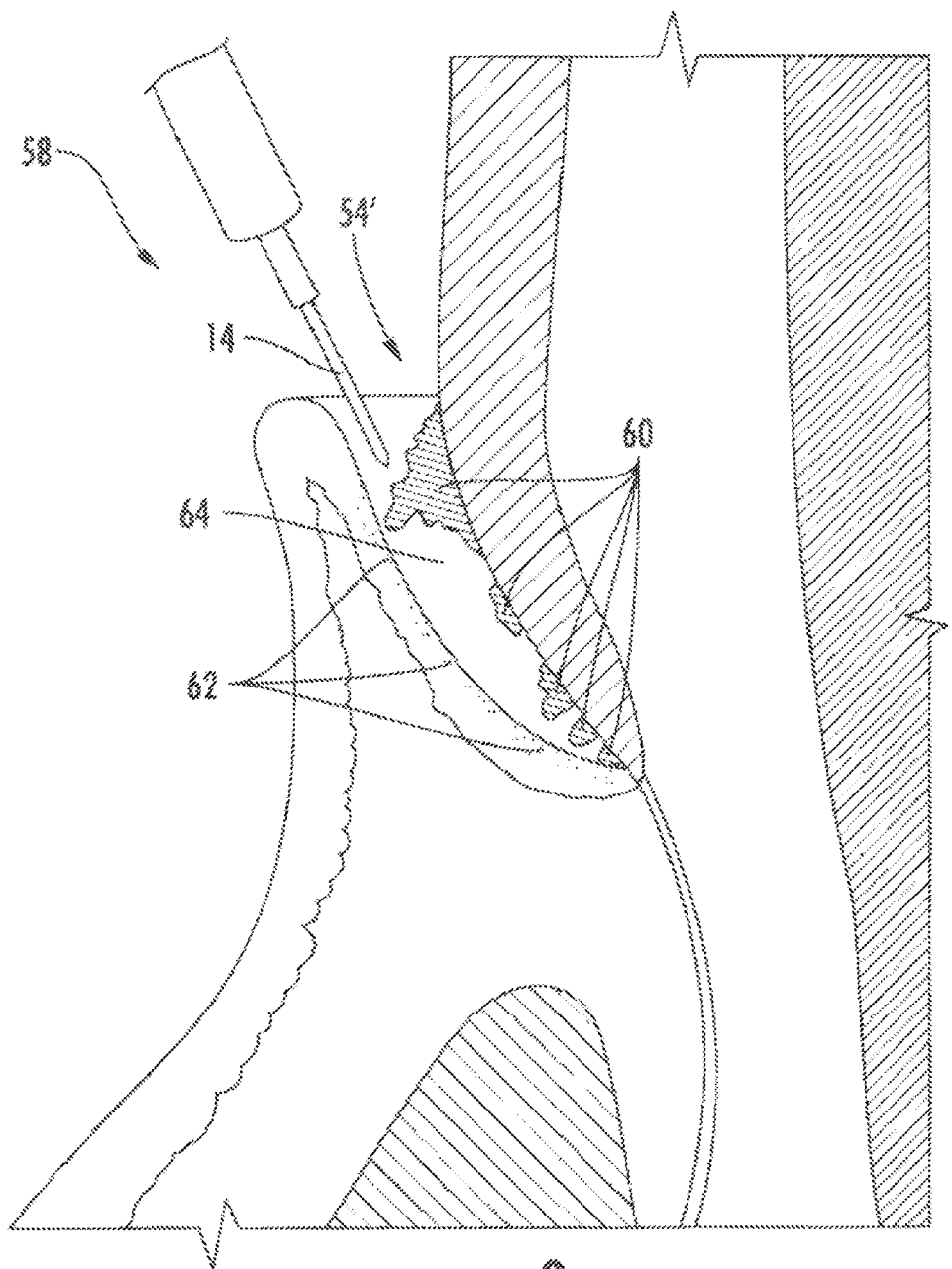
FIG. 8 shows a somewhat schematic cutaway view of a tooth and surrounding gum tissue including a sulcus filled with a fluid mixture in which an instrument has been inserted for treatment.

As shown in FIG. 3B and FIG. 4, the most preferred embodiment of the present invention utilizes an energy source which is preferably a pulsed laser energy that is coupled to a solution in such a fashion that it produces an enhanced photoacoustic pressure wave 8. The laser light is delivered using a commercially available laser source 12 and an optical light fiber 14 attached at a proximate end to the laser source 12 and has an application tip 20 at the distal end. The application tip 20 may be flat or blunt, but is preferably a beveled or tapered tip having a taper angle between 10 and 90 degrees. Preferably any cladding 18 on the optic fiber 14 is stripped from approximately 2-12 mm of the distal end. The taper angle of the fiber tip 20 and removal of the cladding 18 provide wider dispersion of the laser energy 16 over a larger tip area and consequently produces a larger photoacoustic wave. The most preferred embodiment of the application tip 20 includes a texturing or derivatization of the beveled tip 20, thereby increasing the efficacy of the conversion of the laser energy 16 into photoacoustic wave energy within the solution. A coupling ferrule may be used to interchange different applicator tips. It should be noted that in the present invention this tapered tip 20, the surface treatment, and the sheath or cladding 18 stripping is not for the purpose of diffusing or refracting the laser light 16 so that it laterally transmits radiant optical light energy to the root surface. In the current invention these features are for the sole purpose of increasing the photoacoustic wave.

Herein derivatization means a technique used in chemistry that bonds, either covalently or non-covalently, inorganic or organic chemical functional group to a substrate surface.

It was found that the photoacoustic coupling of the laser energy to the solution provides enhanced penetration of the solution into the root canal and accessory canals, thereby allowing the solution to reach areas of the canal system that are not typically accessible.

The photoacoustic (PA) wave is generated when the laser energy transitions from the tip (usually quartz or similar material) of the laser device into the fluid (such as water, EDTA, or the like. The transmission from one medium to another is not 100% efficient and some of the light energy is turned into heat near the transition that the light makes from one media to the other. This heating is very rapid, locally heating some of the molecules of the fluid very rapidly, resulting in molecule expansion and generating the photoacoustic wave. In a pulsed laser, a wave is generated each time the laser is turned on, which is once per cycle. A 10 HZ pulsed laser then generates 10 waves per second. If the power level remains constant, the lower the pulse rate, the greater the laser energy per pulse and consequently the greater the photoacoustic wave per pulse.

The photoacoustic effect creates sound (pressure) waves that can potentially propagate throughout both the media and localized structure, e.g., the main root canal and the lateral or accessory canals. These sound waves provide vibrational energy, which expedites the breaking loose of and/or causing cell lysis of the biotics and inorganics in the root canal and lateral canal systems. In addition these vibrational waves help the propagation of the fluids into and throughout the main and lateral canal systems.

In general, light travels in a straight line, however, in a fluid light can be bent and transmitted around corners, but this transmission is minimal compared to the straight-line transmissibility of light. A sonic or shock wave on the other hand is easily transmitted around corners and through passages in a fluid. For example, air is a fluid. If you stood in one room and shined a bright light from that room into a hallway that was at right angles to that room, the intensity of the light would decrease the farther you go down the hallway. If you then went into a room at the end of the hallway and went to a back corner of the room, the light might be very dim. However, if while standing at the same location as the light source, you yelled vocally at the hallway, you could most likely hear the sound in the back corner of the back room. This is because sound is propagated spherically by the vibration of molecules instead of primarily in a straight line like light.

Although the laser light cannot turn corners easily and cannot propagate easily into the lateral canals, the sonic wave produced by the photoacoustic effect is easily transmitted through the lateral canals. Also, since the canals are tapered in a concave fashion, the photoacoustic wave will be amplified as it transverses toward the end of the lateral canals. Since the cross-sectional area of the lateral canals decreases as the wave traverses toward the canal end, the amplitude of the wave increases much as a Tsunami wave increases as it approaches a beach where the cross sectional area of the water channel constantly decreases.

The tip design can affect the magnitude and direction of the produced photoacoustic wave. A tapered tip has the effect of diverting the laser energy over the larger cone area (compared to the circular area of the standard tip) and thereby creating a larger photoacoustic wave. The same applies to any stripped sheath section of the tip.

Testing Using a MEMS Pressure Sensor:

A small plastic vial was fitted with a fluid connection (bottom of vial at right angles to axis of vial) that was close coupled hydraulically to a miniature MEMS piezo-resistive pressure sensor (Honeywell Model 24PCCFA6D). The sensor output was run through a differential amplifier and coupled to a digital Oscilloscope (Tektronics Model TDS 220). This model oscilloscope will hold a trace on the screen and allow a digital image to be taken of the trace. The vial and sensor were filled with water. The laser tip was submerged below the fluid level in the vial and fired (laser frequency was 10 HZ) at various power setting. A trace was recorded of the resulting photoacoustic pressure waves.

A 170% increase in the photoacoustic wave was observed for the tapered and stripped tip versus the blunt-ended tip. A 580% increase in the photoacoustic wave was observed for textured (frosted) tapered/stripped tip versus the standard blunt-ended tip. The tapered tip has a greater exposed area than the blunt straight tip. The fiber optic is coated with a polyamide sheath, which reflects the laser beam internally, not allowing it to escape and propagating the laser energy down the fiber to the tip. On the straight or blunt-ended tip, the exposed area is the circular cross-sectional area of the end of the tip. On the tapered tip and textured tip the exposed area is the area of the tapered cone, which is greater than the exposed area of the blunt straight tip. This invention is on the ability of these features to increase the photoacoustic wave not to refract or redirect the radiant optical properties of the laser energy. In fact such radiant light energy can fuse the root canal wall surface making it impossible to clean and debride the small passages behind the fused areas.

During a previous experiment, fluid was placed into a Dampen dish located on a Formica surface. The laser tip was placed into the fluid and fired repetitively. The photoacoustic wave vibrated the Dampen dish on the Formica surface making an audible sound. For a specific tip this audible sound increased with an increasing power level of the laser. This implies that the audible sound is somewhat proportional to the amplitude of the photoacoustic wave. This was verified by placing a sound level meter one inch away from the Dampen dish and recording the dB level. Next, the laser power level was held constant and the tip was changed. The tapered and stripped sheath tip produced a greater photoacoustic wave than the standard straight or blunt-end tip. A tapered and stripped tip was then frosted or etched. This tip was tested and showed a greater photoacoustic wave generated than the non-frosted version. This was verified to be true at three different power levels. It would appear that since the power level was held constant, the photoacoustic wave amplitude would also be proportional to the exposed area and the surface treatment.

An increase in photoacoustic wave generation was seen by stripping the polyamide sheath away for 2-12 mm from the tapered end. Although laser light is coherent and travels in a straight line, some light bounces off of the polyamide sheath at an angle. As this light travels down the light path it continues bouncing off of the inside of the polyamide sheath and will eventually exit at an angle to the sheath once the sheath stops and exposes a non sheathed section. Therefore, some of the laser energy would also exit where the polyamide sheath has been removed, just upstream of the tapered tip. A tip with the sheath removed for 2 to 12 mm directly upstream of the tapered section was placed in the above-mentioned test set up.

The photoacoustic wave will propagate primarily perpendicular to the exposed surface and secondarily spherically with respect to the exposed surface. The standard straight end tip would have the PA wave propagating primarily in line with the tip. The tapered tip produced PA wave would be primarily propagated in a more lateral pattern. The tapered tip with the shinned sheath would propagate the PA wave in a more spherical pattern than the other two.

The standard straight blunt end tip would be less desirable because it directs the photoacoustic wave toward the apical end of the tooth and would have more propensities to drive the fluid from the nerve hole in the apical end and outward into the gum which could create medical complications. Since there may be lateral or accessory canals anywhere along the main root canal, it is more desirable to have a spherical wave distribution to direct waves to as many lateral canals as possible. Therefore the tapered tip with the skinned sheath produces a more desirable effect within the tooth.

Resultant Scanning Electron Micrographs (SEM's) show the reticular surface of the dentin to be devoid of infection and malady and allowing for rinsed removal of the debris elements.

A method and apparatus according to a preferred embodiment of the present invention uses a subablative energy source, preferably a pulsing laser, to produce photoacoustic energy waves in solutions dispensed in a root canal to effectively clean the root canal and lateral canals. In the context of this application, the term "subablative" is used to refer to a process or mechanism which does not produce or cause thermal energy-induced destruction of nerve or other native tooth structure, material or tissue, namely, that does not carbonize, burn, or thermally melt any tooth material. The pulsing laser in the inventive configuration of a preferred embodiment induces oscillating photoacoustic energy waves which emanate generally omnidirectionally from adjacent the exposed length of an applicator tip where light energy is caused to exit the surface of optical fiber material in many directions/orientations into adjacent fluid medium from a light energy source maintained at a relatively low power setting of from about 0.1 to no more than about 1.5 watts in order to avoid any ablative effects.

According to one embodiment of the present invention, a tooth is first prepared for treatment in a conventional manner by drilling a coronal access opening in the crown of the tooth to access the coronal or pulp chamber and associated root canal. This may be performed with a carbide or diamond bur or other standard approaches for preparation of a tooth for root canal treatment known in endodontic practice after which the upper region above the entry of the canal into the chamber is generally emptied of pulp and other tissue. Thereafter, a first solution is slowly dispensed into the chamber, such as by use of a syringe or other appropriate mechanisms, with a small amount seeping and/or injected down into the individual root canals containing the as-yet unremoved nerves and other tissue. The first solution is preferably dispensed in an amount sufficient to fill the chamber to adjacent the top of the chamber. In other embodiments, portions of the nerve and other tissue in the canals may be removed using a broach or other known methods for removing a nerve from a root canal before the first solution is dispensed into the chamber and down into the root canals. In some embodiments, only a single solution may be used, although multiple solutions or mixtures may also be used as explained in more detail below.

The first solution preferably includes a compound containing molecules with at least one hydroxyl functional group and/or other excitable functional groups which are susceptible to excitation by a laser or other energy source in the form of rapidly oscillating photoacoustic waves of energy to assist with destructive subablative disintegration of root canal nerve tissue. It has been observed that certain fluids which do not contain excitable groups, such as xylene, do not appear to produce the desired photoacoustic wave when an energy source has been applied. In one embodiment of the invention, the first solution is a standard dental irrigant mixture, such as a solution of water and ethylenediamine tetraacetic acid (EDTA), containing hydroxyl or other excitable groups. In other embodiments of the invention, the hydroxyl-containing solution may be distilled water alone. In other alternate embodiments, solutions containing fluids other than water may be used, or various pastes, perborates, alcohols, foams, chemistry-based architectures (e.g., nanotubes, hollow spheres) and/or gels or a combination of the like may be used. Additionally, various other additives may be included in the solution. For example, and not by way of limitation, the first solution may include agents energizable by exposure to energy waves propagated through the solution from adjacent the fiber. These include materials selected from the group consisting of hydrogen peroxide, perborates, hypochlorites, or other oxidizing agents and combinations thereof. Additional additives believed to be energizable in the solution include materials selected from the group consisting of reducing agents, silanols, silanating agents, chelating agents, chelating agents coordinated or complexed with metals (such as EDTA-Calcium), anti-oxidants, sources of oxygen, sensitizing agents, catalytic agents, magnetic agents and rapidly expanding chemical, pressure or phase change agents and/or combinations of the like. The solution may also include dispersions or mixtures of particles containing nano- or micro-structures, preferably in the nature of fullerenes, such as nanotubes or bucky balls, or other nanodevices (including micro-sized devices) capable of sensitizing or co-acting with oxygenating, energizable, or activatable components in the solution/mixture, such as oxidative bleaching or other oxygenated agents. Various catalytic agents may be titanium oxide or other similar inorganic agents or metals. The first solution may also include additional effective ingredients such as surfactants or surface active agents to reduce or otherwise modify the surface tension of the solution. Such surface active agents may be used to enhance lubrication between the nerves and other intracanal tissue and the canals wall, as well as antibiotics; stabilizers; antiseptics; anti-virals; germicidals; and polar or non-polar solvents; and the like. It is especially preferred that all materials used in the system be bio-compatible and FDA and otherwise approved, as necessary, for use in dental procedures. The amounts of any of the foregoing and other additives are generally very small in the order of a few percent by weight or only small fractions of percents. The majority of the solution/mixture is preferably water, preferably sterile triple distilled water for avoidance of undesirable or unaccounted for ionic effects.

An activating energy source is applied to the first solution contained in the coronal pulp chamber. In a preferred embodiment, the activating energy source is a pulsing laser 10. The laser light energy 16 is delivered using a laser source 12 and an optical light fiber 14 attached at its proximate end to a laser source 12 and having an applicator tip 20 adjacent its distal end. The optical fiber 14 preferably has a diameter of from about 200 microns to about 400 microns. The diameter should be small enough to easily fit into the coronal pulp chamber and, if necessary, into a root canal itself, but large enough to provide sufficient energy via light carried therein to create a photoacoustic effect and to prevent avoidable leakage of light or loss of energy and damage to the tooth or the fiber tip. In a preferred embodiment, the laser source is a solid state laser having a wavelength of from about 700 nm to about 3000 nm, such as NdYAG, ErYAG, HoYag, NdYLF, Ti Sapphire, or ErCrYSGG laser. However, other suitable lasers sources may be used in various embodiments.

An appropriately dimensioned laser applicator tip 20 is preferably placed into the coronal chamber until it is at least fully immersed in the first solution. By "fully immersed" it is meant liquid level is even with the edge of the cladding or other covering on the optical fiber 18. Preferably, the distal most edge of any cladding or covering 18 on the optic fiber 14 adjacent the tip is spaced approximately 2-10 mm from the distal end of the distal end tip or end of the fiber, most preferably about 5 mm therefrom. As a result, up to about 10 mm and most preferably about 5 mm of the distal end of the fiber is uncovered. Preferably, all or substantially all of the length of this uncovered part of the tip end is immersed. If the uncovered part of the applicator tip is not fully immersed, sufficient energy may not be transferred to the fluid since light will be permitted to escape to the environ above the liquid surface. Accordingly, it is believed that spacing the distal-most or outermost end edge of the cladding more than about 10 mm should be avoided, as that can diminish the effectiveness of the system. In some applications, it may be necessary to provide a dam and reservoir around and above the opening in the tooth in order to increase the volume and level of fluid available for immersion of the uncovered area of the end of the fiber. The larger liquid volume and deeper immersion of the uncovered area of the tip end is believed to enable application of sufficient energy levels to produce the desired photoacoustic wave intensity in such instances. Such instances may include, for example, smaller teeth such as upper/lower centrals or teeth that are fractured off. In certain applications where a dam or reservoir is used it may be desirable to use a laser tip with more than 10 mm of space between the tip end and the cladding due to the larger volume of fluid.

It is a feature of the invention in a preferred embodiment that the distal-most end of the applicator tip be tapered to and end point, i.e. that the distal end have a "tapered tip" 22. Most preferably, the tapered tip has an included taper angle of from about 25 to about 40 degrees. The applicator tip 20 is therefore preferably not a focusing lens configured to concentrate light to a point in space away from the tip end. Such a configuration is believed to cause an ablative effect due to the high thermal energy created by the laser light focused to a point. Rather, the taper angle of the tapered fiber tip 22 and rearward spacing of the end of the cladding from the tip end in accordance with preferred embodiments of the invention are believed to enable a relatively wide dispersion of the laser energy for emission from a relatively large surface area of the tip all the way back to the edge of the cladding, not merely from the end of the laser fiber. An objective is to emit laser light generally omnidirectionally from the sides 24 and from the tapered area 22 of the tapered applicator tip, and consequently, to produce a larger or more omnidirectional photoacoustic wave propagating into surrounding liquid and adjacent material from substantially the entire exposed surface of the fiber optic quartz material. Among other things, this avoids and preferably eliminates any ablative effects associated with higher levels of focused or refracted radiant laser energy. The tip design in accordance with the invention is selected to provide a magnitude and direction of the photoacoustic wave in the surrounding fluid medium that exhibits a relatively sharp or high rise time at the leading edge of each pulse and which propagates through the fluid generally omnidirectionally from the exposed area of the end of the fiber. Accordingly, a tapered tip according to the invention has the effect of dispersing the laser energy over the larger uncovered cone surface area and the rearwardly extending cylindrical wall surface (compared to a two dimensional generally flat circular surface area of a standard tip), thereby creating a much larger area through which the leading edges of the successive photoacoustic waves can propagate. In some embodiments, the exposed area of the fiber adjacent the tip end may include a texturing, such as frosting or etching, to increase the surface area and angular diversity of light emission for an even more comprehensive coverage of the photoacoustic wave energy within the solution and adjacent tissue.

When applying the laser to the first solution, applicants have discovered that it may be important to apply the laser energy to the solution so as to limit the creation of thermal energy. In the present invention, after the applicator tip is immersed in the first solution, laser energy is preferably applied to the first solution using subablative threshold settings, thereby avoiding any thermal-induced carbonization, melting, or other effects caused by a temperature rise above about 5° C. in the dentin walls of the canal, apical portions of the tooth, or surrounding bone or tissue caused by the generation of significant thermal energy in the canal area or wall due to the ablative power settings used in prior attempts to perform root canal therapy with lasers. The practice of the present invention in accordance with its preferred embodiments causes an observable temperature rise in the solution of no more than a few degrees Centigrade and, as a result, no more than a few degrees Centigrade elevation, if any, of the dentin wall and other adjacent tooth structure and tissue. This is far below the standard constraint of avoiding any exposure of such material and tissue to more than 5° C. increase in temperature for any significant period of time to avoid permanent damage in the same.

The inventors have found that relatively low power settings of from about 0.1 watt to about 1.5 watt and with a laser pulse duration of from about 100 nanoseconds to about 1000 microseconds, with a pulse length of about 50 microseconds most preferred, produces the desired photoacoustic effect without heating the fluid or surrounding tissue to produce any ablative or other thermal effect within or adjacent the root canal. A frequency of from about 5 to 25 Hz is preferred and a frequency of about 15 Hz is believed to provide optimal potentiation of harmonic oscillation of pressure waves in the fluid medium to disintegrate nerve and other tissue within the canal.

The particular preferred power level found to produce the ideal photoacoustic wave has a relationship to the approximate root volume of a particular tooth. The following chart (Table 1) shows what are believe to be preferred ranges of power levels for treatment of root canals in different types and sizes of teeth in accordance with the invention.

TABLE 1

Preferred Power Levels for Various Tooth Types

| Tooth Type | Approx. Average Root Volume (μL) | Range of Preferred Power Levels (watts) |
|---|---|---|
| Molar | 177 | 0.5 to 1.5 |
| Pre Molar | 88 | 0.5 to 1.0 |
| Cuspid | 67 | 0.5 to 0.75 |
| Laterals | 28 | 0.25 to 0.5 |
| Centrals | 28 | 0.25 to 0.5 |
| Lower Centrals | 28 | 0.1 to 0.25 |

When the laser is immersed in the first solution, the laser is pulsed for a time preferably ranging from about 10 seconds to about 40 seconds, most preferably about 20 seconds. If the laser is pulsed for longer than about 40 seconds, excessive thermal energy can begin to develop in the fluid, potentially leading to deleterious heating effects in and around the tooth as described above. It has been found rather surprisingly that pulsing under the parameters of the invention causes a measurable temperature rise in the fluid medium of no more than a few degrees Celsius, if any, while still utterly destroying and/or disintegrating all nerve, pulp, and other tissue within the canal that also is observed to hydraulically self-eject from the canal during pulsing.

After the laser has been pulsed in the first solution, the first solution is allowed to stabilize and then laser pulsing treatment may be repeated again in the same or a different solution. In certain embodiments, the solution may be removed between repetitions of pulsing cycles of the laser to remove debris more gradually and to avoid any development or transfer of heat energy into the dentin surrounding wall or other adjacent structure. The coronal chamber and canal may be irrigated with a standard dental irrigant and solution may then be reinserted into the coronal chamber to perform an additional laser pulsing treatment. While any number of pulsing phases or cycles can be repeated, it is believed that a fully effective removal of all material within the canal can be achieved in less than about seven cycles.

To assist dentists in performing root canal treatments according to the present invention, a photoacoustic activity index has been developed which provides relationships between the various parameters, machine setting, and the like which have been found to be important in the practice of the inventive procedure. Factors which appear important in the practice of the invention include the power level, laser pulse frequency, the pulse duration, the proportion of average excitable functional groups per molecule in the first solution, the diameter of the laser optical fiber, the number of pulsing cycles repeated in completing an extirpation procedure, the duration of each cycle, the viscosity of the first solution, and the distance between the tip and the end of the cladding. Coefficients have been determined which relate deviations of certain of the above factors from what is believed to be the ideal or the most preferred factor value. Tables of these coefficients are shown below:

| Tooth Type | Approx. Average Root Volume (ul) | Preferred Range of Power Levels (watts) | Power Density Coefficient (DPD) |
|---|---|---|---|
| Molar | 177 | 0.5 to 1.5 | 1 |
| Pre Molar | 88 | 0.5 to 1.0 | 1 |
| Cuspid | 67 | 0.5 to 0.75 | 1 |
| Laterals | 28 | 0.25 to 0.5 | 1 |
| Centrals | 28 | 0.25 to 0.5 | 1 |
| Lower Centrals | 28 | 0.1 to 0.25 | 1 |

| Frequency Coefficient $C(fq)$ | Pulses per Second (Value in HZ) |
|---|---|
| 0.4 | 2 HZ |
| 0.6 | 5 HZ |
| 0.9 | 10 HZ |
| 1 | 15 HZ |
| 0.5 | 20 HZ |
| 0.2 | 25 HZ |

| Pulse Duration Coefficient $C(pw)$ | Pulse Duration Value in micro sec (μs) |
|---|---|
| 1 | <50 |
| 0.9 | 50 |
| 0.7 | 100 |
| 0.3 | 150 |
| 0.2 | 200 |
| 0.1 | 1000 |

| Hydroxyl Coefficient $C(hy)$ | Average quantity of excitable groups per fluid molecule |
|---|---|
| 1 | >2 |
| 0.9 | 2 |
| 0.7 | 1 |
| 0.5 | Part or Mixture |
| 0 | none |

| Fiber Diameter Coefficient $C(fd)$ | Fiber Diameter Value in microns |
|---|---|
| 0.8 | >400 |
| 1 | 400 |
| 0.8 | 320 |
| 0.5 | 200 |
| 0.3 | <200 |

| Repetition Cycle Coefficient $C(rp)$ | Repetition Cycles (repetitions) |
|---|---|
| 0.3 | >7 |
| 0.5 | 6 |
| 0.7 | 5 |
| 1 | 4 |
| 0.9 | 3 |
| 0.6 | 2 |
| 0.3 | 1 |

| Cycle Duration Coefficient $C(sa)$ | Cycle Duration (Value in seconds) |
|---|---|
| 0.2 | >40 |
| 0.6 | 40 |
| 0.9 | 30 |
| 1 | 20 |
| 0.5 | 10 |
| 0.2 | <10 |

| Viscosity Coefficient $C(vs)$ | Fluid Viscosity (Centipoise) |
|---|---|
| 1 | <1 |
| 0.9 | 1 |
| 0.1 | >500 |
| 0.05 | >1000 |

| Cladding Separation Length Coefficient $C(sl)$ | Distance Between Terminus of Cladding and Apex of Tip Value in millimeters (mm) |
|---|---|
| 0.4 | 2 |
| 0.6 | 3 |
| 0.9 | 4 |
| 1 | 5 |
| 0.9 | >5 |
| 0.3 | >10 |

A practitioner may input coefficients from the above tables correlating to equipment, setting, and material parameters into the following equation:

$$\text{Photoacoustic Activity Index("PA" Index)} = DPD \times C(fq) \times C(pw) \times C(hy) \times C(fd) \times C(rp) \times C(sa) \times C(vs) \times C(sl)$$

If the resulting PA Index value is greater than about 0.1, more preferably above about 0.3, then the equipment and materials may generally be acceptable to produce an effective photoacoustic wave for disintegration and substantially complete and facile removal of all root canal nerve, pulp, and other tissue from within the canal. If the PA Index is below about 0.1, it may indicate a need to modify one's equipment setup, setting, and method parameters in order to more closely approach the desired PA index of 1 or unity.

Using the invention parameters and procedures, root canal tissue and other material to be removed or destroyed is not believed to be removed or destroyed via thermal vaporization, carbonization, or other thermal effect due primarily to exposure to high temperatures, but rather through a photoacoustic streaming of and other activities within liquids in the canal which are laser activated via photon initiated photoacoustic streaming (PIPS). A photoacoustic wave with a relatively high leading edge is generated when the laser light transitions from the exposed surface of the fiber optic material into the solution. The laser light is believed to create very rapid and relatively intense oscillations of waves through the solution emanating from the interface of the exposed surface of the fiber optic and the surrounding liquid. The rapid, intense microfluctuations in the light energy emitted is believed to cause rapid excitation and/or expansion and de-excitation and/or expansion of hydroxyl-containing molecules adjacent the exposed surface of the fiber generating, among other things, photoacoustic waves of energy which propagates through and into the root canal system and oscillates within the system. These intense photoacoustic waves are believed to provide substantial vibrational energy, which expedites the breaking loose of and/or cell lysis and other effects to bring about a rapid and facile degradation/disintegration of substantially all tissue in the root canal and lateral canal systems immersed in the solution. The pulsing photoacoustic energy waves in combination with the chemistry of the fluid also is believed to cause intense physically disruptive cycling of expanding and contracting of nerve and other tissue which porositizes, expands, and ultimately disintegrates the nerve and other tissue in the canal without any significant thermally induced carbonization or other thermal effects of the same so that the resulting solution/mixture containing nerve and other tissue remains is observed to be self-ejected or basically "pumped" by a hydraulic effect out of the canal.

The photoacoustic effect creates energy waves that propagate throughout the fluid media in the main root canal and into the lateral canals, thereby cleaning the entire root system. The use of a substantially incompressible fluid medium causes the waves produced by the photoacoustic effect to be instantly transmitted through the lateral canals. Also, since the canals are tapered in a concave fashion, the photoacoustic wave is believed to be amplified as it transverses toward the end of the lateral canals for further intensification of the destruction towards apical or cul de sac areas.

In certain embodiments of the invention, a second dissolution solution may be added to the canal after treatment with the energy source/first solution. This dissolution solution chemically dissolves and/or disintegrates any remaining nerve structure or other debris that may remain in the main canal or in any lateral canals. Preferred dissolution solutions include hypochlorite, sodium hypochlorite, perborate, calcium hydroxide, acetic acid/lubricant/doxycycline and other like nerve tissue or matrix dissolving substances such as chelating agents (EDTA) and inorganic agents such as titanium oxides.

Finally, after desired tissue has been removed from the tooth interior, the canal may be irrigated to remove any remaining debris and remaining solution, and then obturated with a material of choice, such as gutta percha, root canal resin, etc., according to standard practices in the industry.

Qualitative experimentation was performed placing a fluid into a Dampen dish located on a Formica surface. The laser applicator tip was placed into the fluid and fired repetitively. The photoacoustic wave vibrated the Dampen dish on the Formica surface making an audible sound. For a specific tip this audible sound increased with an increasing power level of the laser. This was verified by placing a sound level meter one inch away from the Dampen dish and recording the dB level. This implies that the power level is proportional to the amplitude of the photoacoustic wave. Next, the laser power level was held constant and the tip was changed. The tapered tip and a tip with a stripped sheath produced a greater photoacoustic wave than the standard flat tip. A tapered, stripped tip was then frosted or etched. This tip was tested and showed a greater photoacoustic wave generated than the non-frosted version. This was verified to be true at three different power levels. It would appear that since the power level was held constant, the photoacoustic wave amplitude would also be proportional to the exposed area and the surface treatment.

In a quantitative investigation of the applicator tip a MEMS Pressure sensor was utilized to measure the photoacoustic wave amplitude. This testing has shown a dramatic increase in the photoacoustic wave propagation caused by changes in the geometry and texturing of the tip. The inventors have also discovered that stripping of the cladding from the end of the applicator tip results in increases in the photoacoustic wave effect. In this regard, a small plastic vial was fitted with a fluid connection that was close coupled hydraulically to a miniature MEMS piezo-resistive pressure sensor (Honeywell Model 24PCCFA6D). The sensor output was run through a differential amplifier and coupled to a digital Oscilloscope (Tektronics Model TDS 220). The vial and sensor were filled with water. Laser tips having varying applicator tip configurations were fully submerged below the fluid level in the vial and fired at a frequency of 10 HZ. The magnitude of the photoacoustic pressure waves was recorded by the pressure sensor.

A 170% increase in pressure measured from generation of the photoacoustic waves was observed for the tapered tip versus the standard blunt-ended tip. A 580% increase in pressure measured from generation of the photoacoustic wave was observed for textured (frosted) tapered tips versus the standard blunt-ended tip. Rather than emitting in a substantially linear direction, the frosting disperses the light omnidirectionally causing excitation and expansion of more fluid molecules.

An increase in photoacoustic wave generation was seen by stripping the polyamide sheath away from about 2 mm to about 10 mm from the tapered end. Although laser light is coherent and typically travels substantially in a straight line, some light bounces off of the polyamide sheath at an angle. As this light travels down the light path it continues bouncing off of the inside of the polyamide sheath and will eventually exit at an angle to the sheath once the sheath stops and exposes a non sheathed section. Therefore, some of the laser light would also exit where the polyamide sheath has been removed, upstream of the tapered tip end. A tip with the sheath removed for 2 to 10 mm directly upstream of the tapered section was placed in the above-mentioned test set up and showed markedly better production of photoacoustic waves.

In various other embodiments of the invention, energy sources other than lasers may be used to produce the photoacoustic waves including, but not limited to, other sources of light energy, sonic, ultrasonic, photo-acoustic, thermo-acoustic, micromechanical stirring, magnetic fields, electric fields, radio-frequency, and other exciter mechanisms or other similar forms that can impart energy to a solution. Some of these sources penetrate the tooth structure externally. Additional subablative energy sources may be used to create other types of pressure waves in a solution, such as chemoacoustic waves (shock waves created by rapid chemical expansion creating shock and pressure waves). Such waves can be created for example by loading the nanoparticles with a chemical that expands rapidly upon excitation, coating nanoparticles with a hard shell (e.g., polyvinyl alcohol), and activating the chemistry with an energy source such as optical, ultrasonic, radio-frequency, etc. As the activating chemical expands, pressure builds up in the hard shell, when the shell bursts it creates a shock wave that can propagate throughout the fluid similar to a photoacoustic wave. Additionally, a photoacoustic wave can be the activating energy source for producing the chemoacoustic wave.

Further, the present invention may be used for various procedures other than root canal treatment, such as for treatment of dental caries, cavities or tooth decay. Additionally, the present invention may be usable for treatments of bone and other highly networked material where infection is problematic, e.g. dental implants, bone infection, periodontal disease, vascular clotting, organ stones, scar tissues, etc. Adding a tube structure around the tip which might be perforated and will allow introduction of a fluid around the tip that will allow the photoacoustic waves to be directed into more difficult areas that do not contain fluid volume such as periodontal and gum tissue. This would be considered a type of photoacoustic transmission tube. This application process may also be used in other soft tissue applications where it is necessary to expand the diseased tissue or material to allow more rapid access and penetration to healing agents, chemicals or biologicals; i.e., antibiotics, peptides, proteins, enzymes, catalysts, genetics (DNA, mRNA or RNA or derivatives) or antibody based therapeutics or combinations thereof. In some cases, the present methodology may be used to rapidly dissolve or destroy diseased tissue areas. Additionally, the present invention may be used to expand diseased tissue in an abscess, allowing for extremely rapid and efficient penetration of healing or biological agents. The porosity created in the tissue by photoacoustic waves may allow for rapid infusion with the subsequent chemical species that can impose destruction, healing or cleaning or a combination of these events. The speed of this healing action may allow medical procedures that currently are not viable because of extensive time required for standard healing processes, i.e., sometimes adjacent tissue is infected because the original infection cannot be controlled more rapidly than the infection propagates. In this case, expanding the diseased tissue to enhance porosity may allow near instantaneous access for the medication, e.g., antibiotic or other agents.

Furthermore, the present invention may be applied to begin, construct or stage the activation of cells and/or tissues, including the area of transplantation and use in stem or primordial cells accentuation, their attachment and/or stimulation for growth and differentiation. The present invention is also believed to be usable to activate cells, e.g., progenitor, primordial or stem cells, to promote inherent nascent bone or tissue growth and differentiation, as well as in transplantation where stem or primordial cells are accentuated in their attachment and stimulated for growth and differentiation.

In one of the alternate embodiments of this invention, nanotubes or other micro-structures can be moved around in a therapeutic fluid by applying a magnetic field. An alternating or pulsed magnetic field could impart significant motion and stirring of the therapeutic fluid. Since the field would penetrate the entire tooth, the stirring action would also occur throughout the lateral or accessory canal system. These moving micro-particles would also act as an abrasive on any bacteria, virus, nerve material, or debris within the canal system. The effect would be a more thorough circulation of the fluid throughout the canal system to provide superior cleaning and debridement of the canal system. Magnetic material can also be inserted into, adsorbed onto, or absorbed into the nanotube or other microstructure increasing its magnetic moment.

$TiO_2$ or other similar compounds can be activated and made bactericidal by exposing them to UV light or by inserting them in an electric field. Once excited these can destroy bacteria and other organic compounds such as remaining nerve tissue. Such compounds can be part of a therapeutic and can be activated by a UV light source pointed toward the therapeutic fluid, a UV source dipped into the fluid, or a UV laser source. These $TiO_2$ or other similar compounds can also be activated by an alternating or pulsed electric field. One means to supply such an electric field could be by an external device that would bridge the tooth. Since the field propagates throughout the entire tooth it would also react $TiO_2$ or other similar compounds within the accessory or lateral canals. This action could also be combined with the micro-particle based motion action mentioned above. This combination would more thoroughly clean and debride the canals. Since electric fields are generated externally and penetrate the entire root structure they could be used several months or on a yearly basis after the tooth is sealed to reactivate the titanium oxide and its bactericidal properties.

The foregoing description of preferred embodiments for this disclosure has been presented for purposes of illustration and description. The disclosure is not intended to be exhaustive or to limit the various embodiments to the precise form disclosed. Other modifications or variations are possible in light of the above teachings. The embodiments are chosen and described in an effort to provide the best illustrations of the principles of the underlying concepts and their practical application, and to thereby enable one of ordinary skill in the art to utilize the various embodiments with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for cleaning a root canal of a tooth, the method comprising:
   delivering a treatment liquid into the root canal;
   inserting a tip of an optical fiber into the treatment liquid within the root canal, the optical fiber extending along a fiber axis, the tip comprising a conical tip that emits at least a portion of laser light laterally outwardly relative to the fiber axis;
   operating a laser source to generate laser light;
   pulsing the laser light along the optical fiber to the tip; and
   directing at least a portion of the laser light laterally outwardly relative to the fiber axis into the treatment liquid, the laser light emanating from the tip having sufficient power to create photoacoustic waves in the treatment liquid of sufficient vibrational energy to remove at least organic material from a portion of a wall of the root canal.

2. The method of claim 1, further comprising distributing the treatment liquid throughout the root canal with the vibrational energy of the photoacoustic waves.

3. The method of claim 1, wherein the root canal comprises at least a main root canal and a plurality of accessory canals that branch from the main root canal, the method further comprising inserting the tip of the optical fiber into the treatment liquid in the main canal, and propagating the photoacoustic waves throughout the main root canal and the accessory root canals to remove at least organic material from both the main root canal and one or more of the accessory root canals without the tip of the optical fiber being inserted into any of the accessory canals.

4. The method of claim 1, wherein directing at least a portion of the laser light laterally outwardly relative to the fiber axis into the treatment liquid comprises directing most of the laser light in a direction that is non-parallel to the fiber axis.

5. The method of claim 1, wherein inserting the tip of the optical fiber comprises providing the optical fiber having a cladding stripped from a distal end of the optical fiber by a distance in a range of 2 mm to 12 mm.

6. A method for cleaning a tooth having a coronal pulp chamber and a root canal extending from the coronal pulp chamber, the method comprising:
   delivering a treatment liquid into at least the coronal pulp chamber;
   inserting a tip of an optical fiber into the treatment liquid to position the tip within the coronal pulp chamber and outside of the root canal, the optical fiber extending along a fiber axis, the tip comprising a tapered tip without a focusing lens;
   operating an ErCrYSGG laser source to generate laser light;
   pulsing the laser light along the optical fiber to the tip and into the treatment liquid with the tip positioned within the coronal pulp chamber and outside of the root canal; and
   producing photoacoustic waves in the treatment liquid with energy provided by the pulsed laser light, at least a portion of the photoacoustic waves propagating laterally outwardly relative to the fiber axis, the photoacoustic waves of sufficient vibrational energy to remove at least organic material from the coronal pulp chamber.

7. The method of claim 6, further comprising providing a shape for the tip which tapers radially inwardly and distally.

8. The method of claim 7, wherein providing the shape comprises providing a conical tip that tapers to an apex.

9. The method of claim 6, wherein pulsing the laser light involves delivering power at a level sufficient to remove the organic material from the coronal pulp chamber without carbonizing, burning, or thermally damaging dentin along a wall of the coronal pulp chamber with the tip immersed within the liquid.

10. The method of claim 6, wherein pulsing the laser light involves delivering power at a level sufficient to remove the organic material from the coronal pulp chamber without elevating a temperature of the tooth or adjacent tissue by more than 5° C.

11. The method of claim 6, wherein operating the ErCrYSGG laser source comprises operating the ErCrYSGG laser source at a power level in a range of 0.1 W to 1.5 W.

12. The method of claim 6, wherein operating the ErCrYSGG laser source comprises operating the ErCrYSGG laser source at a pulse frequency in a range of 2 Hz to 25 Hz.

13. The method of claim 6, wherein operating the ErCrYSGG laser source comprises operating the ErCrYSGG laser source at a cycle time of 10 seconds to 40 seconds.

14. A method for cleaning a root canal of a tooth, the root canal comprising a main root canal and a plurality of accessory canals that branch from the main root canal, the method comprising:
   delivering a treatment liquid into the root canal;
   inserting a tip of an optical fiber into the treatment liquid within the main root canal, the optical fiber extending along a fiber axis, the tip comprising a tapered tip;
   operating a laser source to generate laser light;
   pulsing the laser light along the optical fiber to the tip; and
   directing at least a portion of the laser light laterally outwardly relative to the fiber axis into the treatment liquid, the laterally directed light having sufficient power to create photoacoustic waves in the treatment liquid of sufficient vibrational energy to remove at least organic material from both the main root canal and one or more of the accessory root canals, without the tip of the optical fiber being inserted into any of the accessory canals.

15. The method of claim 14, wherein directing the at least a portion of the laser light laterally outwardly comprises providing a shape for the tip which tapers radially inwardly and distally.

16. The method of claim 14, wherein directing at least a portion of the laser light laterally outwardly relative to the fiber axis into the treatment liquid comprises directing most of the laser light in a direction that is non-parallel to the fiber axis.

17. The method of claim 14, wherein inserting the tip of the optical fiber comprises providing the optical fiber having a cladding stripped from a distal end of the optical fiber by a distance in a range of 2 mm to 12 mm.

\* \* \* \* \*